US012226454B2

(12) United States Patent
Cheng et al.

(10) Patent No.: US 12,226,454 B2
(45) Date of Patent: Feb. 18, 2025

(54) PHARMACEUTICAL COMPOSITIONS AND USE THEREOF FOR RELIEVING ANTICANCER DRUG RESISTANCE AND ENHANCING SENSITIVITY OF ANTICANCER DRUG

(71) Applicant: Rise Biopharmaceuticals Inc., Beijing (CN)

(72) Inventors: Jya-Wei Cheng, Tainan (TW); Hsi-Tsung Cheng, Tainan (TW); Hui-Yuan Yu, Tainan (TW); Su-Ya Hsu, Tainan (TW)

(73) Assignee: RISE BIOPHARMACEUTICALS INC., Beijing (CN)

( * ) Notice: Subject to any disclaimer, the term of this patent is extended or adjusted under 35 U.S.C. 154(b) by 1058 days.

(21) Appl. No.: 17/085,480

(22) Filed: Oct. 30, 2020

(65) Prior Publication Data

US 2021/0060130 A1    Mar. 4, 2021

Related U.S. Application Data

(63) Continuation-in-part of application No. 17/006,512, filed on Aug. 28, 2020, which is a continuation-in-part of application No. 15/569,033, filed as application No. PCT/CN2015/008725 on Jun. 3, 2015, now abandoned.

(60) Provisional application No. 62/959,553, filed on Jan. 10, 2020, provisional application No. 62/927,829, filed on Oct. 30, 2019.

(51) Int. Cl.
  *A61K 38/19*  (2006.01)
  *A61P 35/00*  (2006.01)
  *A61K 31/5377*  (2006.01)

(52) U.S. Cl.
  CPC ............ *A61K 38/195* (2013.01); *A61P 35/00* (2018.01); *A61K 31/5377* (2013.01)

(58) Field of Classification Search
  None
  See application file for complete search history.

(56) References Cited

U.S. PATENT DOCUMENTS 5,595,756 A * 1/1997 Bally .................. A61K 9/1272
                                                    264/4.1

FOREIGN PATENT DOCUMENTS

| CN | 101200502 A | 6/2008 |
| CN | 102596227 A | 7/2012 |
| EP | 0616615 A1 | 9/1994 |

OTHER PUBLICATIONS

Heppner et al. (Cancer Metastasis Review 2:5-23; 1983) (Year: 1983).*
Sporn et al ("Chemoprevention of Cancer," Carcinogenesis, vol. 21 (2000), 525-530 (Year: 2000).*
Auerbach et al (Cancer and Metastasis Reviews, 2000, 19: 167-172) (Year: 2000).*
Gura T (Science, 1997, 278(5340): 1041-1042, encloses 1-5) (Year: 1997).*
Jain RK (Scientific American, Jul. 1994,58-65) (Year: 1994).*
Hait (Nature Reviews/Drug Discovery, 2010, 9, pp. 253-254) (Year: 2010).*
Gravanis et al. (Chin Clin Oncol, 2014, 3(2):22, pp. 1-5) (Year: 2014).*
Beans (PNAS 2018; 115(50): 12539-12543) (Year: 2018).*
Bowie, James U. et al., "Deciphering the Message in Protein Sequences: Tolerance to Amino Acid Substitutions", Science, vol. 247, Mar. 16, 1990, pp. 1306-1310.
Burgess et al., "Possible dissociation of the heparin-binding and mitogenic activities of heparin-binding (acidic fibroblast) growth factor-1 from its receptor-binding activities by site-directed mutagenesis of a single lysine residue", Journal of Cell Biology, vol. 111, Issue 5, Nov. 1, 1990, pp. 2129-2138.
Jain, RK, "Barriers to Drug Delivery in Solid Tumors," Scientific American, vol. 271, Issue 1, Jul. 1994, pp. 58-65.
Gura, T, "Systems for identifying new drugs are often faulty", Science, vol. 278(5340), Nov. 7, 1997, pp. 1041-1042.
Lazar et al., "Transforming Growth Factor a: Mutation of Asparatic Acid 47 and Leucine 48 Results in Difference biological Activies". Molecular and Cellular Biology, vol. 8, Issue No. 3, Mar. 1998, pp. 1247-1252.
Bork, Peer, "Powers and Pitfalls in Sequence Anayalsis" The 70& Hurdle, Genome Research, vol. 10, Issue No. 4, 2000, pp. 398-400, 2000.
Sporn, Michael et al., "Chemoprevention of Cancer," Carcinogenesis, vol. 21, Issue No. 3, Mar. 2000, pp. 525-530.
Auerbach, Robert et al. Angiogenesis assays: Problems and pitfalls:, Cancer and Metastasis Reviews, Issue 19, Jun. 1, 2000, pp. 167-172.
Le, Y.Y. et al., "Chemokines and Chemokine Receptors: their Maniold Roles in Homeostasis and Disease", Cellular & Molecular Immunology, Apr. 30, 2004, vol. 1, Issue No. 2., pp. 95-101.

* cited by examiner

*Primary Examiner* — Brian Gangle
*Assistant Examiner* — Andrea K McCollum
(74) *Attorney, Agent, or Firm* — Muncy, Geissler, Olds & Lowe, P.C.

(57) ABSTRACT

The present invention provides a novel modified chemokine peptide. The novel modified chemokine peptide can be combined with a targeted drug for treating cancer, especially for treating drug-resistant cancer, and inhibiting tumor growth more effectively.

3 Claims, 23 Drawing Sheets

Specification includes a Sequence Listing.

PHARMACEUTICAL COMPOSITIONS AND USE THEREOF FOR RELIEVING ANTICANCER DRUG RESISTANCE AND ENHANCING SENSITIVITY OF ANTICANCER DRUG

CROSS-REFERENCE TO RELATED APPLICATIONS

This application claims priority in U.S. Provisional Patent Application No. 62/927,829, filed Oct. 30, 2019, which is incorporated by reference in its entirety herein.

This application is also a continuation-in-part of U.S. application Ser. No. 17/006,512 filed on Aug. 28, 2020, which is a Continuation-in-Part of U.S. application Ser. No. 15/569,033, filed on Oct. 24, 2017, which claims the benefit of this is a National Phase Application filed under 35 U.S.C. 371 as a national stage of PCT/CN2015/080725, filed Jun. 3, 2015, the content of which is hereby incorporated by reference in its entirety.

FIELD OF THE INVENTION

The present invention relates to a pharmaceutical composition. In particular, the present invention relates to a pharmaceutical composition for relieving anticancer drug resistance and enhancing sensitivity of anticancer drug.

More specifically, the invention furthermore pertains a pharmaceutical composition comprising a targeted drug combined with a chemokine analogue peptide for overcoming anti-cancer agent resistance, treating drug-resistant cancer and patients with drug resistant cancer and inhibiting tumor growth or/and metastasis.

BACKGROUND OF THE INVENTION

With rapid population growth and aging worldwide, the rising prominence of cancer as a leading cause of death partly reflects in many countries. That is, cancer incidence and mortality are rapidly growing worldwide.

Anticancer therapy is indispensable for cancer treatment. On the other hand, cancer often develops resistance to anticancer therapy. Once a cancer cell acquires resistance to an anti-cancer agent, the cell frequently shows resistance to another anti-cancer agent unused in treatment. In other words, drug resistance is an enormous problem for cancer treatment.

For example, the tyrosine kinase inhibitors (TKIs) are standard treatment in the clinic for patients with advanced EGFR mutant non-small-cell lung cancer (Sharma S V, 2007). First generation EGFR-TKI Gefitinib (brand name Iressa®) would resulted in a significant improvement in outcome for NSCLC patients with activating EGFR mutation. However, after a median duration of response for 12 months, all patients developed tumor resistance, and in over half of these patients this is due to the emergence of the EGFR T790M resistance mutation (Wheeler D L, 2010).

Additionally, ELR-CXC chemokine is associated with angiogenesis accompanied upon tumor development, and its inductive mechanism is the activation generated by conjugating this type of chemokine, especially referring to CXCL8, with CXCR1 and CXCR2 on the endothelial cells (ECs). At present, it is proved that many different types of tumors are able to secret ELR-CXC chemokines. For example, one or more ELR-CXC chemokines were indicated to confer resistance to EGFR inhibitors by inducing stein cell properties in cancer (Liu Y N, 2015).

Unfortunately, the therapeutic effects do not always last, as the tumors develop resistance mutations that are not susceptible to existing drugs. In other words, although there are many different anti-tumoral preparations used in clinical practice, their efficiency is in most cases insufficient and the range of diseases sensitive to such therapy is limited.

Thus, new, more active preparations, and the development of such compositions which are effective in treating and preventing tumors with primary and gained resistance, remains of current interest in this invention.

It is therefore attempted to deal with the above situation encountered in the prior art by this invention.

SUMMARY OF THE INVENTION

An object of the invention is to provide an agent/a medicament/a pharmaceutical composition for overcoming drug resistance, or an agent/a medicament/a pharmaceutical composition for overcoming anti-cancer agent resistance.

Another aspect of the present invention provides methods of treating cancer, methods of treating drug-resistant cancer, and pharmaceutical compositions for use in treating cancer in subjects such as those with drug-resistant cancer.

Another aspect of the present invention provides a method for treating a cancer in an individual comprising administering to the individual a combination therapy which comprises one or more chemokine analogue peptides and one or more medicaments.

Other embodiments provide use of a chemokine analogue peptide in the manufacture of medicament for treating a cancer in an individual when administered in combination with a targeted drug, a pharmaceutically acceptable buffer, diluent, carrier, adjuvant or excipient; and use of a targeted drug, a pharmaceutically acceptable buffer, diluent, carrier, adjuvant or excipient in the manufacture of a medicament for treating a cancer in an individual when administered in combination with a chemokine analogue peptide.

Detailed description of the invention is given in the following embodiments with reference to the accompanying drawings.

DETAILED DESCRIPTION OF THE INVENTION

Figure 1:
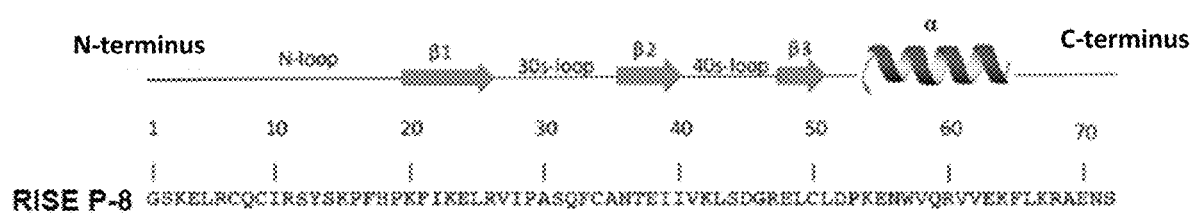
FIG. 1 shows the full-length amino acid sequence and structure of RISE P-8.
Figure 2A:
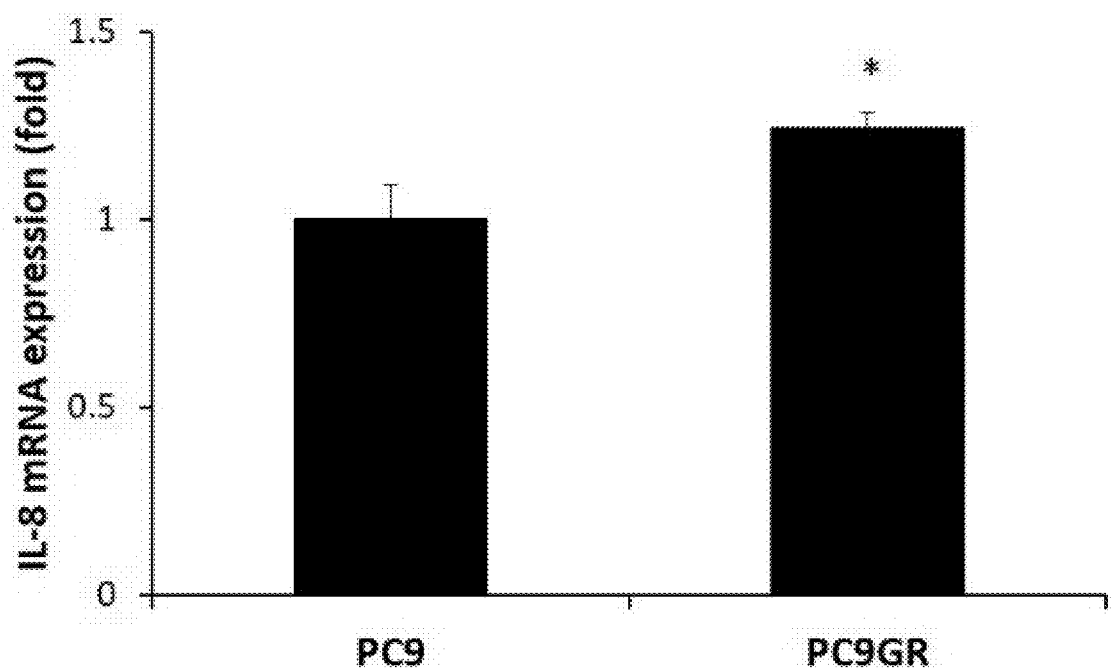
FIG. 2A-2D depict CXCL8, CXCR1 and CXCR2 mRNA expression of parental cells and Gefitinib-resistant cells.
Figure 2B:
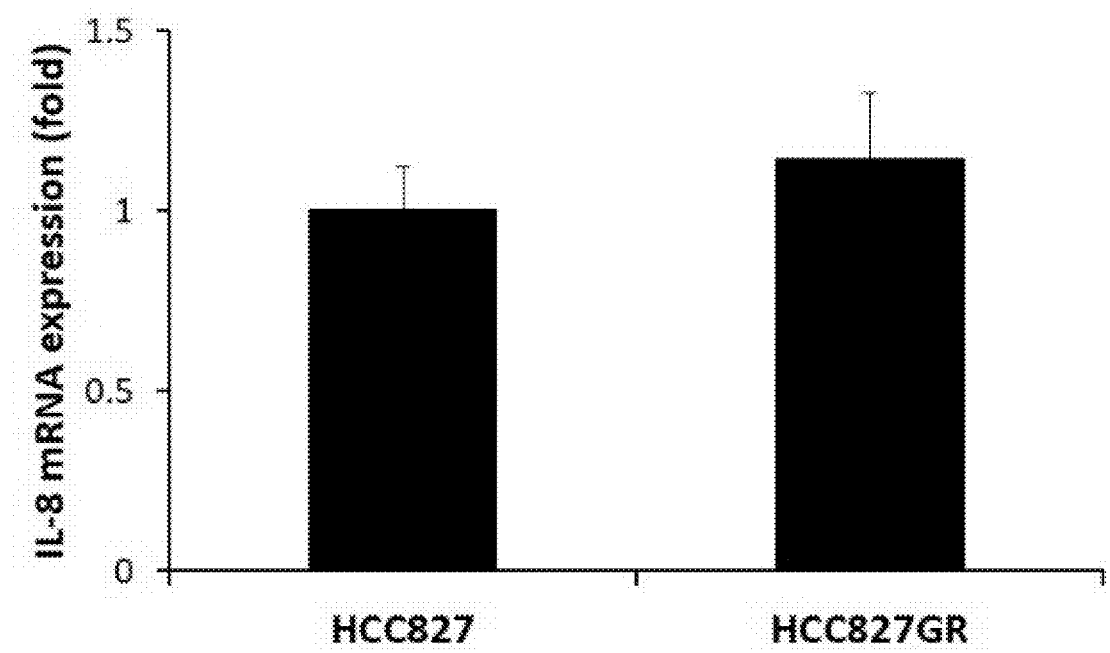
Figure 2C:
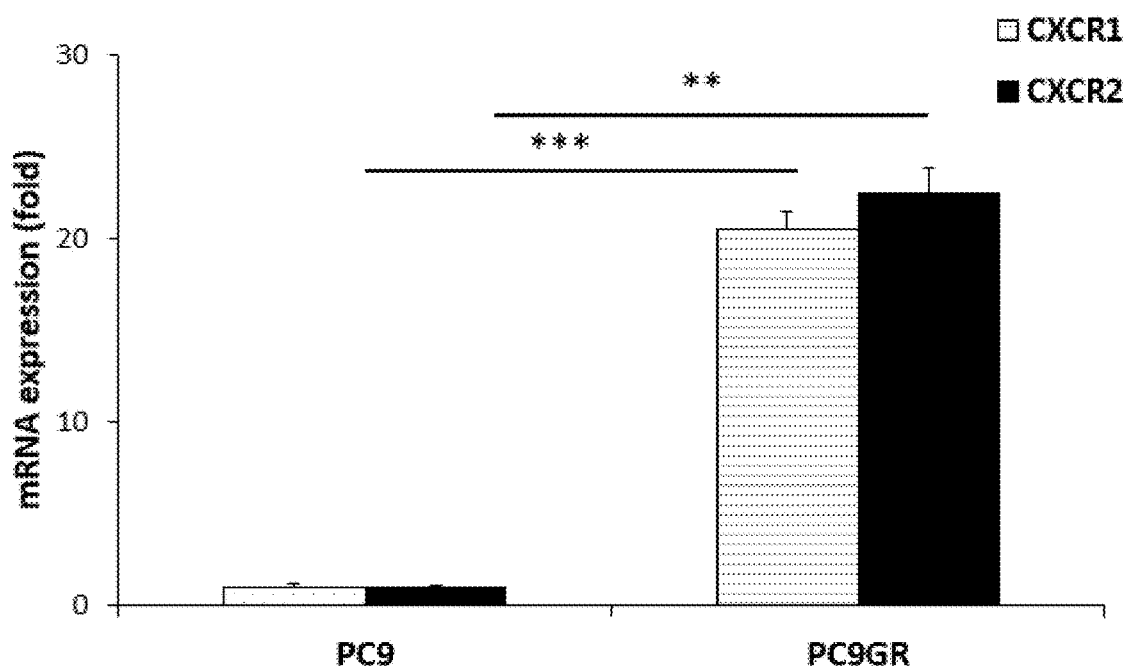
Figure 2D:
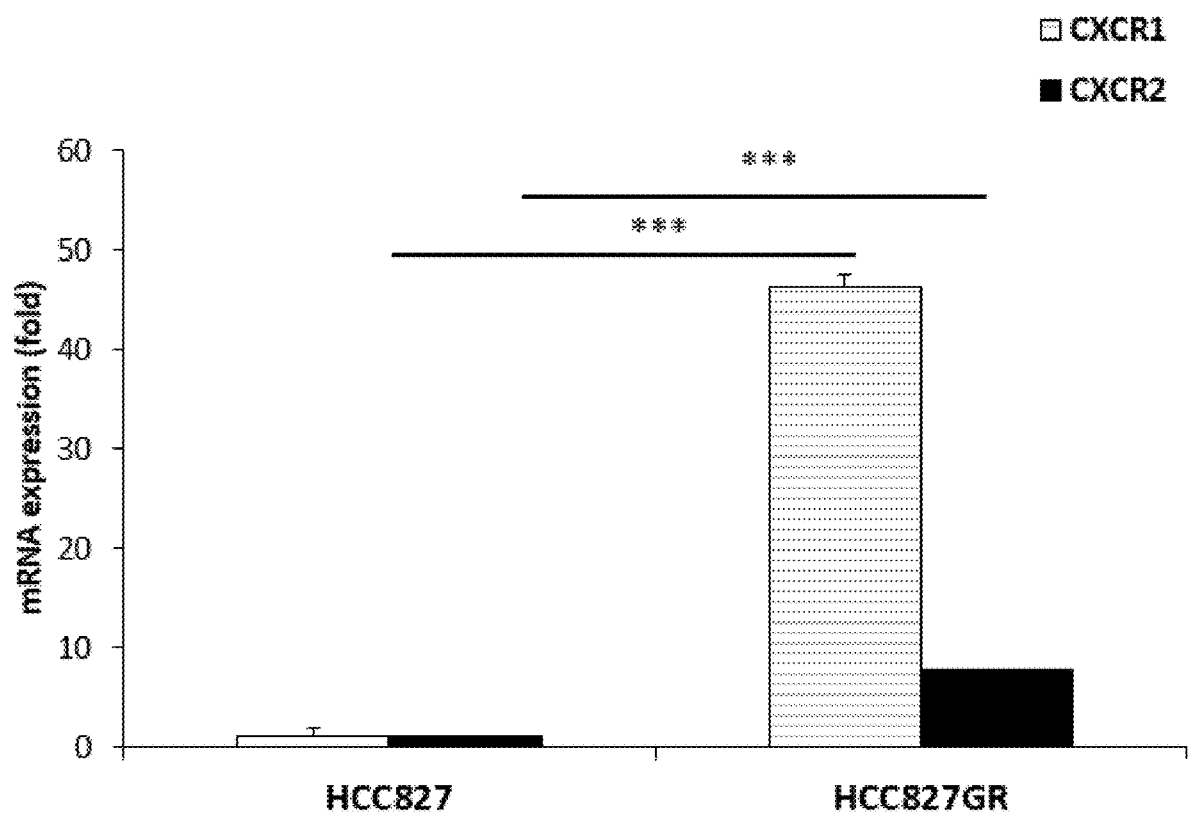

Before the present invention is described in further detail, it is to be understood that the detailed description and specific examples, while indicating embodiments of the invention, are given by way of illustration only, since various changes and modifications within the spirit and scope of the invention will become apparent to those skilled in the art. One skilled in the art, based upon the description herein, can utilize the present invention to its fullest extent. Unless defined otherwise, all technical and specific terms used herein have the same meaning as commonly understood by one of ordinary skill in the art to which the invention belongs.

The following definitions are meant to clarify, but not limit, the terms defined. If a particular term used herein is not specifically defined, such term should not be considered indefinite. Rather, terms are used within their accepted meanings by those of skill in the art.

The term "pharmaceutical combination" or "combination" as used herein means the combined administration of the therapeutic agents, which can be a chemokine analogue peptide or/combined with a targeted drug. In the context of the present invention, the therapeutic agents include a chemokine analogue peptide or/combined with a targeted drug that can be administered independently at the same time or separately within time intervals such that these time intervals allow the combination partners to exhibit a synergistic effect.

The term "synergistic" or "synergistic effect" as used herein refers to the therapeutic effect achieved with the combination of the present invention and/or through the method of treating cancer of this invention; which is greater than the sum of the effects that result from using the chemokine analogue peptide and the targeted drug alone or separately. Advantageously, such synergy between the therapeutic agents allows for the use of smaller doses of one or both therapeutic agents, provides greater efficacy at the same doses, and/or prevents or delays building up of drug resistance. The synergistic effect can be achieved either by co-formulating the therapeutic agents contained in the pharmaceutical combination or the composition as described herein or administering the said therapeutic agents simultaneously through a unit dosage form or as separate formulations administered simultaneously or sequentially.

The term "therapeutically effective amount" as used herein means an amount of a chemokine analogue peptide or/combined with a targeted drug effective in producing the desired therapeutic response in a particular patient (subject) suffering from cancer. Particularly, the term "therapeutically effective amount" includes the amount of the therapeutic agents, which when administered will achieve the desired therapeutic effects. In the context of the present invention the desired therapeutic effects includes partial or total inhibition, delay or prevention of the progression of cancer including cancer metastasis; inhibition, delay or prevention of the recurrence of cancer including cancer metastasis; and/or the prevention of the onset or development of cancer in a subject. In respect of the therapeutic amount of the therapeutic agents i.e. the chemokine analogue peptide or/combined with the targeted drug, consideration is also given that the amount of each of the therapeutic agent used for the treatment of a subject is low enough to avoid undesired or severe side effects, within the scope of sound medical judgment. The therapeutically effective amount when used in combination will vary with the age and physical condition of the end user, the severity of cancer, the duration of the treatment, the nature of any other concurrent therapy, the specific type of therapeutic agent employed for the treatment, the particular pharmaceutically acceptable carrier utilized in the pharmaceutical compositions containing the therapeutic agents and other relevant factors.

The term "subject" as used herein refers to an animal, particularly a mammal, and more particularly, a human. The term "mammal" used herein refers to warm-blooded vertebrate animals of the class "Mammalia", including humans. The term mammal includes animals such as cat, dog, rabbit, cattle, horse, sheep, goat, monkey, mouse, rat, gerbil, guinea pig, pig and the human. The term "subject" may be used interchangeably with the term patient. In the context of the present invention the phrase "a subject in need thereof" means a subject in need of the treatment for cancer. Alternatively, the phrase "a subject in need thereof" means a subject (patient) diagnosed with cancer.

"Treating" or "treatment" as used herein refers to the treating or treatment of a disease or medical condition (such as cancer, tumor, neoplasm conditions) in a subject/patient, such as a mammal (particularly a human or a companion animal) which includes ameliorating the disease or medical condition, i.e., eliminating or causing regression of the disease or medical condition in a subject/patient; suppressing the disease or medical condition, i.e., slowing or arresting the development of the disease or medical condition in a subject/patient; or alleviating the symptoms of the disease or medical condition in a subject/patient.

The term "pharmaceutically acceptable" as used herein means the carrier, diluent, excipient, and/or salt used in the composition should be compatible with the other ingredients of the formulation, and not deleterious to the recipient thereof. "Pharmaceutically acceptable" also means that the compositions or dosage forms are within the scope of sound medical judgment, suitable for use for a subject such as an animal or human without excessive toxicity, irritation, allergic response, or other problems or complication, commensurate with a reasonable benefit/risk ratio.

"Clinical benefit" refers to a phrase used by doctors and/or clinicians treating cancer. The term encompasses any appreciated or perceived benefit encountered by a subject/patient during therapy. As used herein, the term includes but is not limited to one or more of clinical benefit is one or more of decrease in tumor size, suppression or decrease of tumor growth, delayed time to progression, no new tumor or lesion, a decrease in new tumor formation, an increase in survival or progression-free survival, and no metastases.

According to one aspect, the present invention provides a pharmaceutical composition for relieving anticancer drug resistance and enhancing sensitivity of anticancer drug, which comprises a chemokine analogue peptide at least. In addition, the pharmaceutical composition further comprises a targeted drug.

Optionally, in an exemplary embodiment of the present invention, the chemokine analogue peptide of the present invention includes, but are not limited to, RISE P-8 (SEQ ID NO: 1).

Sequences of RISE P-8 (SEQ ID NO: 1) which can be employed in accordance with the invention are shown hereinbelow:

GSKELRCQCIRSYSKPFHPK-
   FIKELRVIPASQFCANTEIIVKLSDGREL-
   CLDPKENWVQRVVEKFLKRAENS         SEQ ID NO: 1:

Furthermore, RISE P-8 was designed as an analogous protein of CXCL8 (IL-8) and became the antagonist of CXCR1 and CXCR2. The complete amino acid sequence and protein structure of RISE P-8 are shown in FIG. 1.

In one embodiment, RISE P-8 directly binds to IL-8 (CXCL8), thereby inhibiting the binding of IL-8 to its receptors CXCR1 and CXCR2 in the present invention.

In another embodiment, the pharmaceutical composition further comprises a medicament, wherein the medicament comprises a targeted drug, a pharmaceutically acceptable buffer, diluent, carrier, adjuvant or excipient.

The aforementioned targeted drugs of the present invention include antibody for cell surface receptor (or antigen), small molecule inhibitors of signaling pathway, mTOR signaling pathway inhibitor, anti-angiogenic agent and proteasome inhibitors. Preferably, the targeted drug is a small molecule inhibitors of signaling pathway.

The antibodies for cell surface receptor (or antigen) include, but not limited to, anti-CD20 monoclonal antibody Rituximab (Mabthera), anti-HER2/neu antibody Trastuzumab (Herceptin) and anti-HER1/EGFR antibody Cetuximab (Erbitux).

The small molecule inhibitors of signaling pathway include, but not limited to, EGFR-TK inhibitors (e.g. gefitinib, dasatinib, erlotinib (Tarceva), imatinib, Nilotinib (Tasigna), lapatinib, sorafenib, sunitinib, afatinib, osimertinib (TAGRISSO) and/or derivants thereof), c-kit tyrosine kinase inhibitor and/or BCR-ABL tyrosine kinase inhibitors (e.g. imatinib, nilotinib, dasatinib, VOTRIENT (Pazopanib)).

The anti-angiogenic agents include, but not limited to, anti-VEGF antibody, e.g. Avastin (Bevacizumab), vascular endothelial growth factor receptor (VEGFR) inhibitors (e.g. Sorafenib, Sunitinib, Vandetanib).

The mTOR signaling pathway inhibitors, include, but not limited to, Temsirolimus and Everolimus.

The proteasome inhibitors include, but not limited to, bortezomib, carfilzomib, marizomib, ixazomib, oprozomib, and delanzomib.

There is no special restriction on the weight ratio, volume ratio and concentration ratio between chemokine analogue peptide and targeted drug. One skilled in the art can select appropriate ratios between chemokine analogue peptide and targeted drug according to the disease, particularly a chemokine analogue peptide when combined with a targeted drug exhibits synergistic effect. In an embodiment, the chemokine analogue peptide administrations are from about 0.01 mg/kg to about 500 mg/kg subject (patient) weight once to three times per week.

In addition, the present invention provides the use of a pharmaceutical composition for relieving anticancer drug resistance and enhancing sensitivity of anticancer drug, and the pharmaceutical composition for treating cancer, inhibiting cancer cell growth and/or inhibiting cancer cell metastasis.

The pharmaceutical composition of the present invention can inhibit the angiogenesis-related diseases or the angiogenesis-dependent diseases of a subject. The angiogenesis-related diseases or the angiogenesis-dependent diseases include, but not limited to, vascular invasion and abnormal cell proliferation, e.g. tumor or cancer. The cancers in the present invention include, but not limited to, chest cancer, abdominal cancer, gastrointestinal cancers, head and neck cancer, brain cancer, endocrine cancer, urologic cancer, male reproductive system neoplasm, gynecologic cancer, blood cancer, skin cancer, and sarcoma.

The chest cancers are selected from lung cancer, including small cell lung cancer (SCLC) and/or non-small cell lung cancer (NSCLC). The NSCLC can be selected from pulmonary adenocarcinoma, squamous cell carcinoma and/or large cell carcinoma. The SCLC can be selected from small cell carcinoma and mixed small cell/large cell cancer or combined small cell lung cancer.

The abdominal cancers include, but not limited to, liver cancer, colorectal cancer, pancreatic cancer, kidney cancer (renal cell cancer), stomach cancer (gastric cancer), adrenocortical cancer, primary peritoneal cancer, peritoneal mesothelioma.

The gastrointestinal cancers include, but not limited to, esophageal cancer, stomach cancer (gastric cancer), liver cancer (hepatocellular carcinoma), gallbladder & biliary tract cancer, pancreatic cancer, colorectal cancer, small bowel cancer, and anal cancer.

The head and neck cancers include, but not limited to, laryngeal and hypopharyngeal cancer, nasal cavity and paranasal sinus cancer, nasopharyngeal cancer, oral and oropharyngeal cancer, and salivary gland cancer.

The types of brain tumors include primary brain tumors or secondary brain tumors. The brain tumors include, but not limited to, astrocytoma, glioblastoma, medulloblastoma, oligodendroglioma, glioma, and brain metastases.

The endocrine cancers include, but not limited to, adrenal tumors, neuroendocrine tumors, parathyroid tumors, pituitary tumors, and thyroid disorders.

The urologic cancers include, but not limited to, bladder cancer and urethral cancer.

The male reproductive system neoplasm include, but not limited to, prostate carcinoma, penile carcinoma, testicular seminoma, and testicular embryonal carcinoma.

The gynecologic cancers include, but not limited to, cervical cancer, ovarian cancer, uterine cancer (endometrial cancer), vaginal cancer, and vulvar cancer.

The blood cancers include, but not limited to, leukemia, Hodgkin lymphoma, non-Hodgkin lymphoma and multiple myeloma.

The skin cancers include, but not limited to, basal cell skin cancer, squamous cell skin cancer, melanoma skin cancer and Merkel cell skin cancer.

The sarcoma includes, but not limited to, soft tissue sarcoma, osteosarcoma (bone sarcoma), and rhabdomyosarcoma.

The neoplasm or/and cancer further include, but not limited, breast cancer, and neuroblastoma.

In an embodiment, the chemokine analogue peptide or/combined with the targeted drug can be administered by conventional routes of administration including, but not limited to oral, intravascular, intradermal, transdermal, intramuscular, intraperitoneal, intratumoral, parenteral, nasal, rectal, sublingual, topical, aerosol, or intratrach.

In an embodiment, the chemokine analogue peptide and/or one or more of the targeted drug(s) can be administered in a form suitable for oral administration such as tablets, lozenges, aqueous or oily suspensions, granules, powders, cachets, emulsions, capsules, syrups, elixirs and the like.

In another embodiment, the chemokine analogue peptide and/or one or more of the targeted drug(s) can be administered parenterally such as, by intramuscular, intrathecal, subcutaneous, intraperitoneal, intravenous bolus injection or intravenous infusion. Parenteral administration can be accomplished by incorporating the chemokine analogue peptide and/or the targeted drug(s) into a solution or suspension.

In one embodiment, the chemokine analogue peptide and/or one or more of the targeted drug(s) can be administered in the form of a pharmaceutical composition containing the said chemokine analogue peptide and/or one or more of the targeted drug(s) and at least one pharmaceutically acceptable diluent, excipient or carrier.

The pharmaceutical composition comprises a chemokine analogue peptide and/or at least one targeted drug and one or more pharmaceutically acceptable diluent, excipient or carrier. For the production of pills, tablets, coated tablets and hard gelatin capsules, the pharmaceutically active excipients that can be used include, but not limited to, lactose, corn starch or derivatives thereof, gum arabica, magnesia or glucose, etc. For soft gelatin capsules and suppositories, the carriers that can be used include, but not limited to, fats, waxes, natural or hardened oils, etc. Suitable carriers for the production of solutions, are, for example injection solutions, or for emulsions or syrups are, for example, water, physiological sodium chloride solution, Phosphate Buffered Saline (PBS), or alcohols, for example, ethanol, propanol or glycerol, sugar solutions, such as glucose solutions or mannitol solutions, or a mixture of the various solvents which have been mentioned. The pharmaceutically acceptable diluents, excipients or carriers used in the pharmaceutical composition can conventionally known pharmaceutically acceptable diluents, excipients or carriers, which can be selected depending on the dosage form and the route of administration of the chemokine analogue peptide and/or the targeted drug(s).

In general, compositions intended for pharmaceutical use can be prepared according to any method known in the art for the manufacture of pharmaceutical compositions.

The compositions described herein can be in a form suitable for oral administration, for example, solid dosage forms such as tablets, capsules, lozenges, or granules; liquid dosage forms such as, emulsions, solutions, suspensions; for parenteral injection (including intravenous, subcutaneous, intramuscular, intravascular or infusion) for example as a sterile solution, suspension or emulsion; for topical administration for example as an ointment, cream, gel or lotion.

Compositions for oral administrations can be in the form of tablets, lozenges, aqueous or oily suspensions, granules, powders, cachets, emulsions, capsules, syrups, or elixirs. Compositions suitable for oral administration can include standard vehicles. Such vehicles are preferably of pharmaceutical grade.

For ointments and creams, the active ingredient (chemokine analogue peptide and/or targeted drug(s)) can be formulated in oil-in-water or water-in-oil base.

For intramuscular, intraperitoneal, subcutaneous and intravenous use, sterile solutions of the active ingredient (chemokine analogue peptide and/or targeted drug(s)) are usually employed, and the pH of the solutions should be suitably adjusted and buffered.

Further, the anticancer effect of chemokine analogue peptide and/or targeted drug(s) contained in the pharmaceutical composition can be delayed or prolonged through a proper formulation.

Although the effective doses of the chemokine analogue peptide and/or targeted drug(s) used for administration vary depending on the severity of the disease (cancer), the severity of symptoms, the age, sex, body weight and sensitivity difference of the subject (the patient), the mode, time, interval and duration of administration, the nature and type of formulation, etc. In certain embodiments, the chemokine analogue peptide and/or one or more targeted drug(s) can be administered in a time frame where both the agents are still active. One skilled in the art would be able to determine such a time frame by determining the half life of the administered therapeutic agents. As indicated herein before, in the pharmaceutical combination and/or the method of treatment of cancer and/or the use for the treatment of cancer according to the present invention the chemokine analogue peptide and one or more targeted drug(s) can be administered simultaneously or sequentially and when administered sequentially in any order. In another embodiments, the chemokine analogue peptide and targeted drug(s) can be administered in the manner that the peak pharmacokinetic effect of one agent coincides with the peak pharmacokinetic effect of the other.

However, the chemokine analogue peptide or/and targeted drug(s) of the invention may alternatively be for use in combination with one or more additional cancer treatments. For example, the chemokine analogue peptide or/and targeted drug(s) may be used in combination with one, two, three, four, five or more additional cancer treatments.

By "in combination" the present invention include that the pharmaceutical composition is administered to a subject who is receiving one or more additional cancer treatments in the same course of therapy. Thus, the term covers not only the concomitant administration of the pharmaceutical composition with one or more additional cancer treatments (e.g., either as bolus doses or infusions) but also the temporally separate administration of these cancer treatments. For example, the pharmaceutical composition may be administered within a treatment schedule/cycle as defined by the patient's oncologist to include one or more additional cancer treatments, administered either before, concomitantly with or after the pharmaceutical composition depending on any of a variety of factors, e.g., severity of the symptoms, etc.

In another embodiment, a therapeutically effective amount of a chemokine analogue peptide or/and targeted drug(s) for treatment of a specific cancer depends on the type and nature of the cancer, its size, progress, and metastatic state, and should be determined at consultation with a physician in charge.

For example, in some embodiments, the pharmaceutical composition of the present disclosure is administered once per month, twice per month, three times per month, every other week, once per week, twice per week, three times per week, four times per week, five times per week, six times per week, every other day, daily, twice a day, or three times a day.

Whilst the dosage of the pharmaceutical composition used will vary according to the activity of the particular chemokine analogue peptide and the condition being treated, it may be stated by way of guidance that a dosage selected in the range from 0.01 to 500 mg/kg per body weight per dose, particularly in the range from 0.02 to 1 mg/kg of body weight per dose. On the other side, this dosage regime may be continued for however many days is appropriate to the patient in question, the daily dosages being divided into several separate administrations if desired.

Representative, nonlimiting acceptable doses for the chemokine analogue peptide administrations are from about 0.01 mg/kg to about 500 mg/kg subject (patient) weight once to three times per week.

Representative, nonlimiting acceptable doses for gefitinib administrations are about 250 mg/kg subject (patient) weight once per day.

Representative, nonlimiting acceptable doses for osimertinib (TAGRISSO) administrations are about 80 mg/kg subject (patient) weight once per day.

Representative, nonlimiting acceptable doses for afatinib administrations are about 40 mg/kg subject (patient) weight once per day.

Representative, nonlimiting acceptable doses for erlotinib (Tarceva) administrations are about 150 mg/kg subject (patient) weight once per day.

Representative, nonlimiting acceptable doses for Mabthera (Rituximab) administrations are from about 90 mg/m$^2$ to about 120 mg/m$^2$ for body surface area per dose.

Representative, nonlimiting acceptable doses for Herceptin (Trastuzumab) administrations are about 2 mg/kg subject (patient) weight per week.

Representative, nonlimiting acceptable doses for oral administrations of VOTRIENT (Pazopanib) are about 800 mg/kg subject (patient) weight once per day.

Representative, nonlimiting acceptable doses for imatinib administrations are from about 400 mg/kg to about 800 mg/kg subject (patient) weight per day.

Representative, nonlimiting acceptable doses for Nilotinib (Tasigna) administrations are from about 400 mg/kg to about 800 mg/kg subject (patient) weight per day.

In one embodiment, the combinations provided by this invention have been evaluated in certain assay systems, and in several different administrative schedules in vitro. The experimental details are as provided herein below. The data presented herein clearly indicate that the chemokine analogue peptide particularly a RISE P-8 when combined with a target drug exhibits synergistic effect. Furthermore, in one embodiment, the subject achieves a clinical benefit.

Additional specific embodiments of the present invention include, but are not limited to the following:

EXAMPLE 1

Cell lines

Lewis lung carcinoma (LL/2) is a cell line established from the lung of a C57BL mouse bearing a tumor resulting from an implantation of primary Lewis lung carcinoma. This lung cancer cell lines grow in Dulbecco's Modified Eagle's Medium with 10% FBS, 1% penicillin-streptomycin, and 1% L-Glutamine in a humidified cell culture incubator at 37° C. in 5% $CO_2$ The human NSCLC cell lines, PC9, Gefitinib-resistant PC9 (PC9GR), HCC827 and Gefitinib-resistant HCC827 (HCC827GR), were maintained in RPMI 1640 medium supplemented with 10% fetal bovine serum, 1% penicillin-streptomycin, and 1% L-Glutamine in a humidified cell culture incubator at 37° C. in 5% $CO_2$. After thawing frozen GR cell lines one week, cells were added 3 μM Gefitinib as final concentration in growth medium for 48 hr to confirm its resistance, then changed fresh growth medium to keep.

EXAMPLE 2

Quantitating Expression Level of CXCR1, CXCR2 and CXCL8 Genes

Total RNA from cells was isolated by RNA Extraction Reagent (REzol™ C & T, Protech Technology Enterprise Co., Taiwan) and quantified by spectrophotometer (Nanodrop 1000, Thermo Scientific). Single-stranded cDNA was synthesized using PrimeScript RT Reagent Kit (Perfect Real Time) (RR037A, TAKARA Bio, Japan) according to the user manuals.

All real-time PCR reactions were performed with 2×qPCR BIO Probe Mix Hi-ROX reagent (PCR Biosystems, UK) and UPL probe system (IL-8, CXCR1, CXCR2) by an StepOnePlus™ Real-Time PCR System (Applied Biosystems™). 18 s was used as an internal loading control. Sequences of the primers included: 5'-gagcactccataaggcacaaa-3' (SEQ ID NO: 2) (forward primer for CXCL8) and 5'-atggttccttccggtggt-3' (SEQ ID NO: 3) (reverse primer for CXCL8); 5'-gaccaacatcgcagacacat-3' (SEQ ID NO: 4) (forward primer for CXCR1) and 5'-tgcttgtctcgttccacttg-3' (SEQ ID NO: 5) (reverse primer for CXCR1); 5'-ggctaagcaaaatgtgatatgtacc-3' (SEQ ID NO: 6) (forward primer for CXCR2) and 5'-caaggttcgtccgtgttgta-3' (SEQ ID NO: 7) (reverse primer for CXCR2). The gene expression was calculated by the following formula: gene expression=$2^{-\Delta\Delta Ct}$.

EXAMPLE 3

Validating Gefitinib-Resistant Cancer Cell Lines

To validate the establishment of Gefitinib-resistant NSCLC cell lines, MTT of Gefitinib gradient was implemented with parental and Gefitinib-resistant (GR) cells, the drug-tolerance of GR cell lines show much higher than parental cells by 100-1000 order (Table 1). The IC50-value of Gefitinib in PC9 cells was 0.6009 μM, as compared to 92.43 μM in PC9GR cells (154-fold resistance); the IC50-value of Gefitinib in HCC827 cells was 0.056 μM, as compared to 125.5 μM in HCC827GR cells (1517-fold resistance).

TABLE 1

| Cell lines | Cytotoxicity of Gefitinib in parental and Gefitinib-resistant cell lines. | | Fold resistance |
|---|---|---|---|
| | IC$_{50}$ (μM) | | |
| | Parental cells | Resistant cells | |
| PC9 | 0.6009 | 92.43 | 153.8 (fold) |
| HCC827 | 0.056 | 125.5 | 2241.1 (fold) |

EXAMPLE 4

Expression Level of CXCL8, CXCR1 and CXCR2 Genes With/Without Gefitinib-Induced in Gefitinib-Resistant Cancer Cells Compared with in Parental Cancer Cells Please refer to FIG. 2A-2D, it shows IL-8 mRNA expression of almost the same or no significantly difference between parental cells (PC9 (FIG. 2A) and HCC827 (FIG. 2B)) and GR cells (PC9GR (FIG. 2A) and HCC827GR (FIG. 2B)). However, CXCR1 mRNA and CXCR2 mRNA expression of GR cells (PC9GR (FIG. 2C) and HCC827GR (FIG. 2D)) compared with parental cells significantly enhance by almost 10-50 times respectively. *P<0.05; P<0.01; *P<0.001, student's t-test.

Figure 3A:
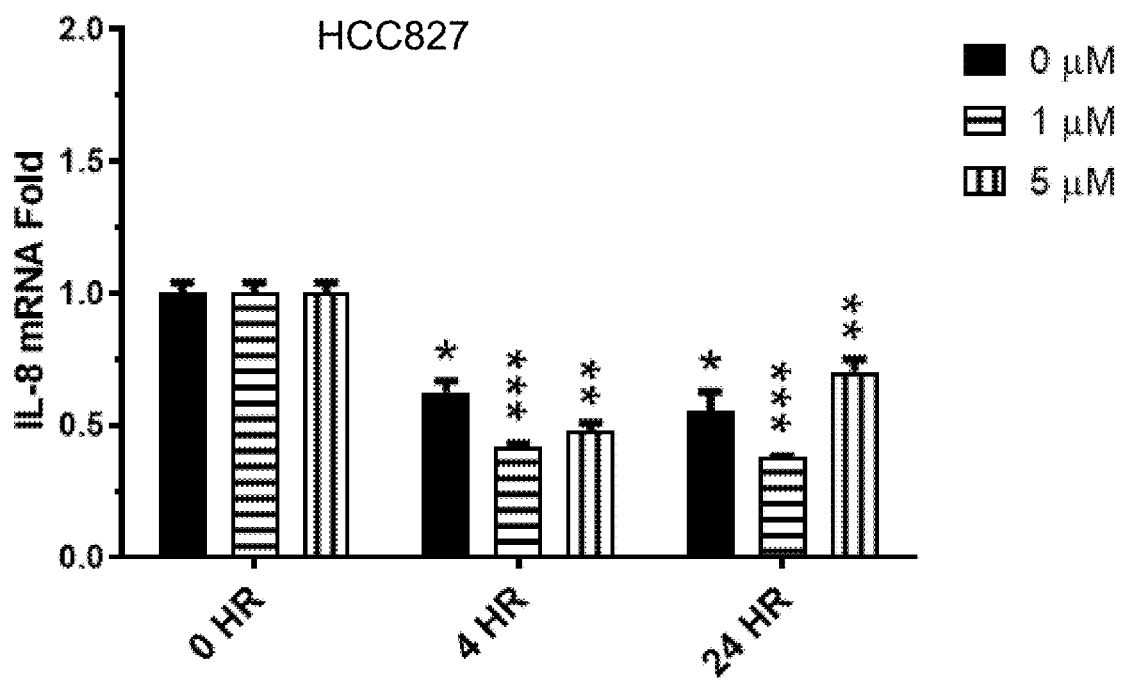
FIG. 3A-3B illustrate IL-8 mRNA expression of parental cells and Gefitinib-resistant cells via gefitinib administrated
Figure 3B:
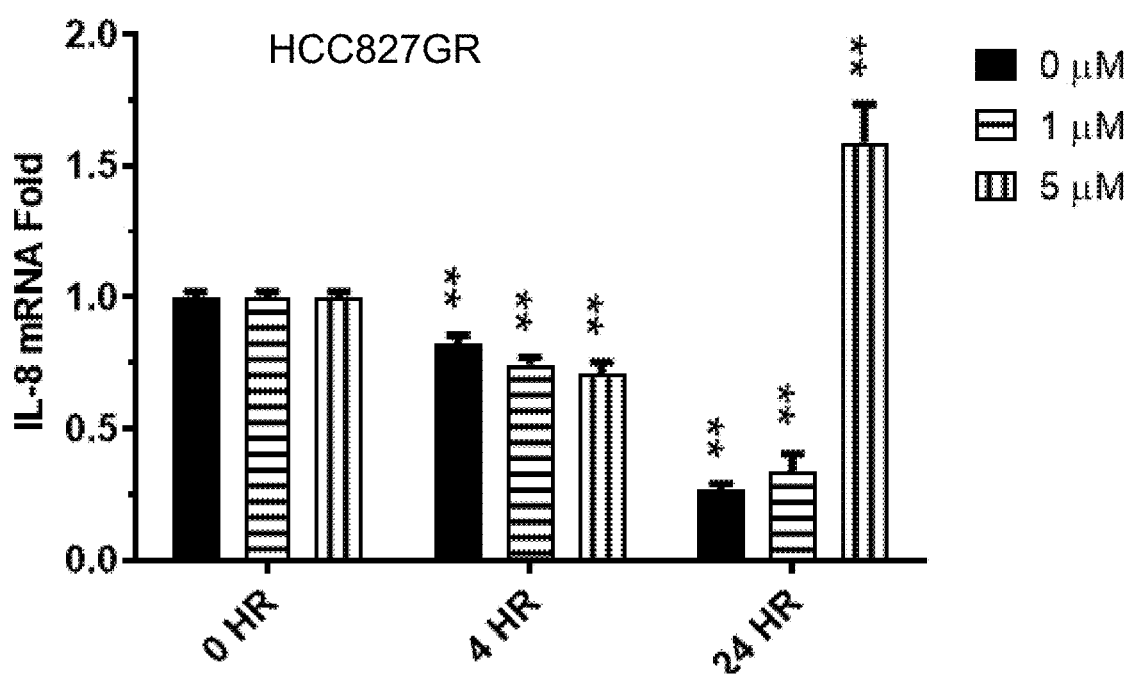

Further, the present invention also illustrated the IL-8 mRNA expression of HCC827 and HCC827GR via gefitinib stimulated. The data showed that IL-8 mRNA expression was not induced obviously in HCC827 after gefitinib-treated (FIG. 3A). On the contrast, IL-8 mRNA expression of HCC827GR increased via gefitinib (5 μM) treated after 24 hours (FIG. 3B).

Figure 4A:
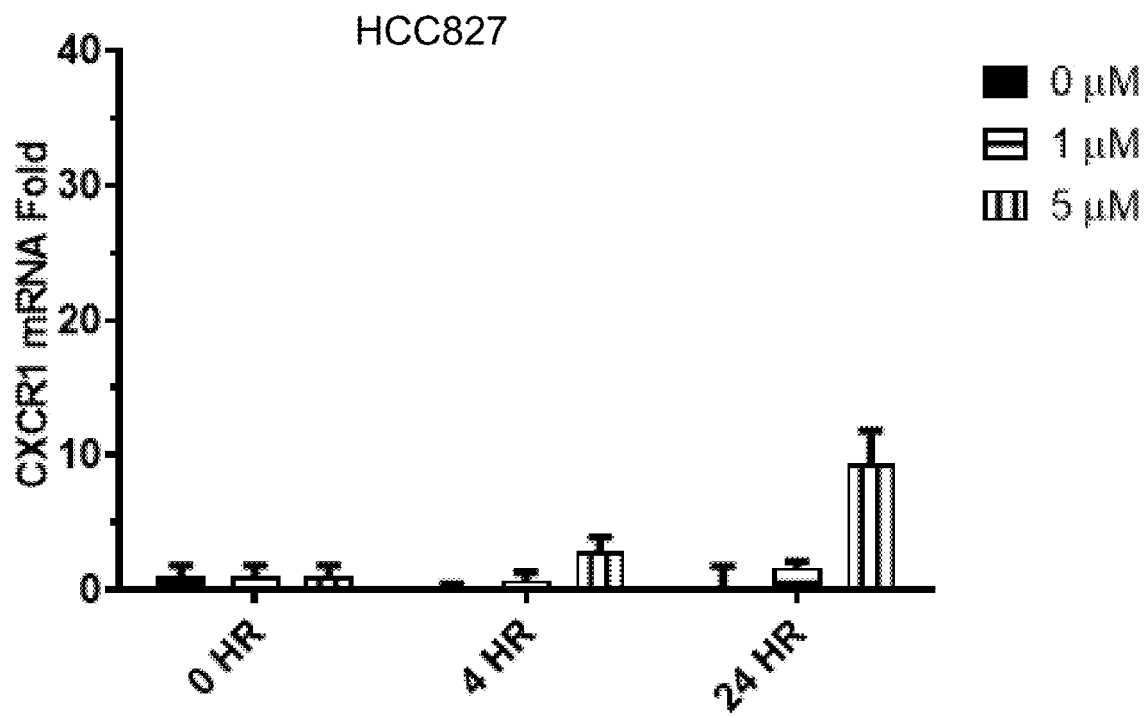
FIG. 4A-4D illustrate CXCR1 and CXCR2 mRNA expression of parental cells and Gefitinib-resistant cells via gefitinib administrated
Figure 4B:
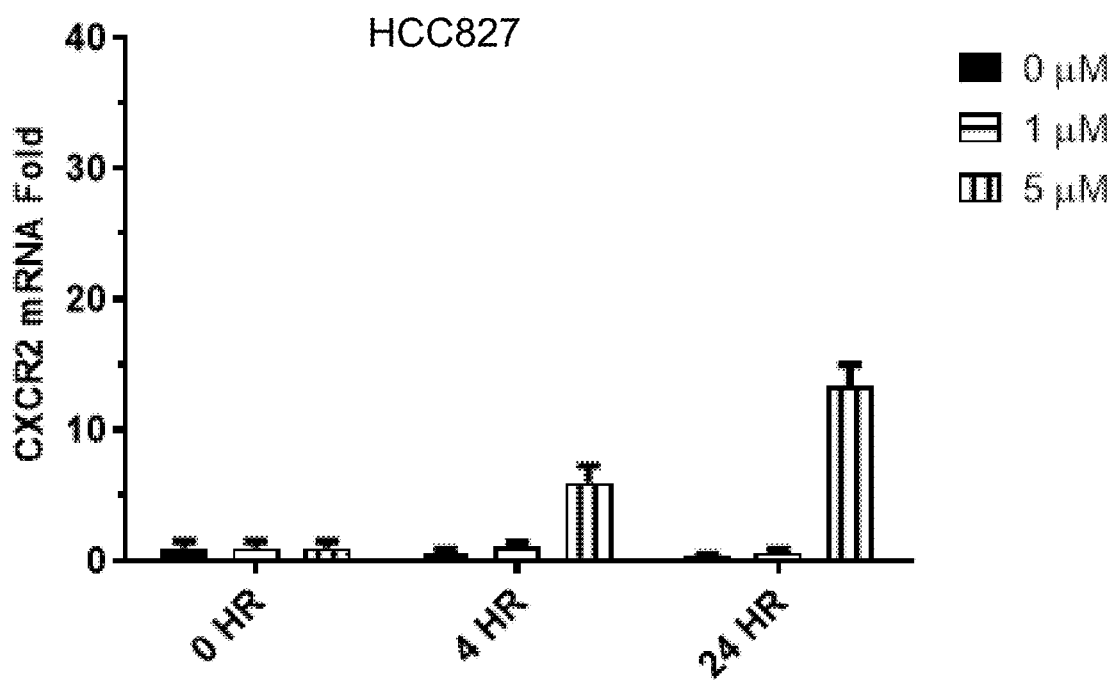
Figure 4C:
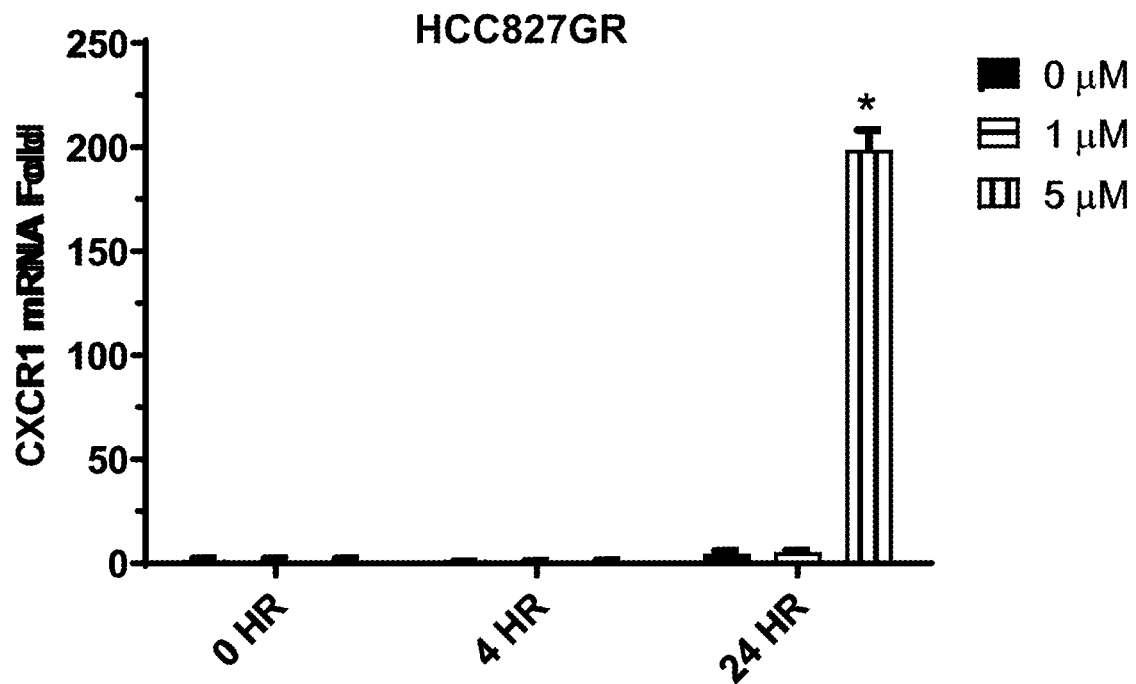
Figure 4D:
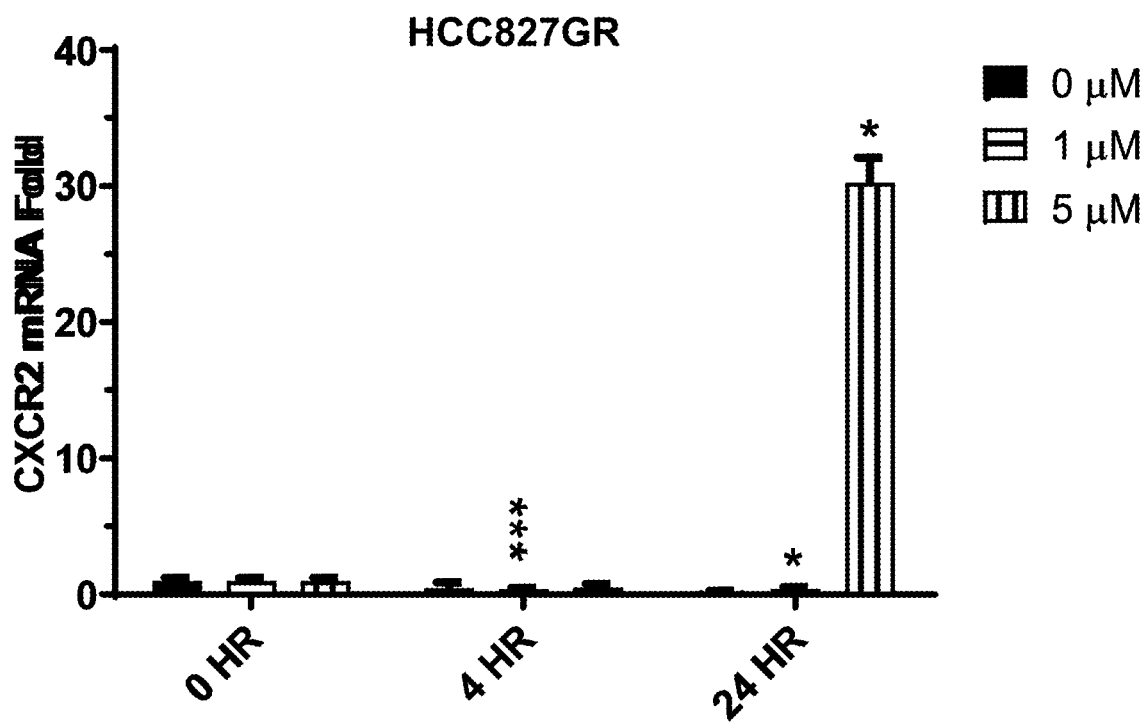

Similarly, the data of CXCR1 and CXCR2 mRNA expression of HCC827 and HCC827GR via gefitinib stimulated were showed that CXCR1 and CXCR2 mRNA expression was not induced obviously in HCC827 after gefitinib-treated (FIG. 4A and FIG. 4B). On the contrast, CXCR1 and CXCR2 mRNA expression of HCC827GR increased via gefitinib (5 μM) treated after 24 hours (FIG. 4C and FIG. 4D).

EXAMPLE 5

RISE P-8 Affect Human Neutrophil Chemotaxis via CXCL8

Figure 5:
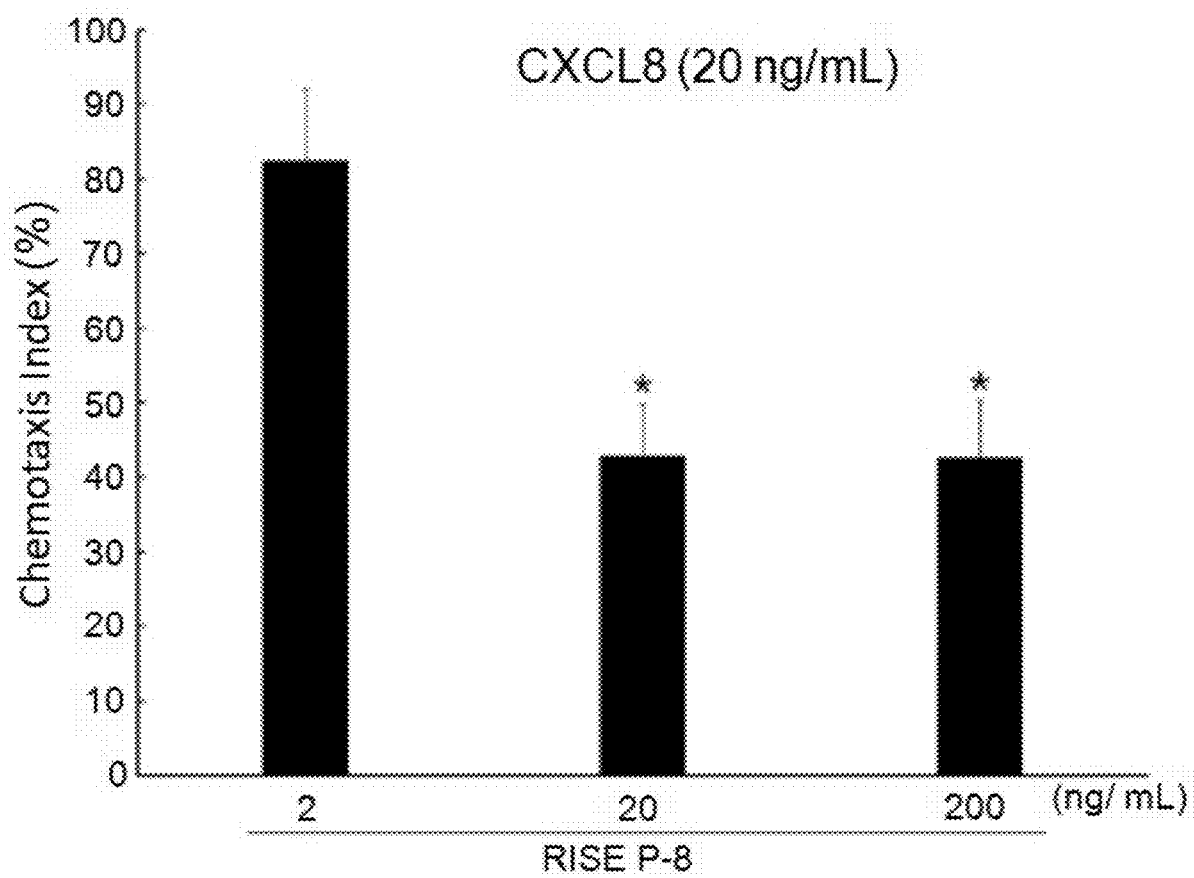
FIG. 5 is a graphic representation of RISE P-8 antagonizing human neutrophil responses via a CXCL8.

Please refer to FIG. 5, neutrophil chemotaxis was assessed using modified Boyden chamber microchemotaxis assays. The CXCL8 alone or combined with RISE P-8, were placed in the lower compartment of the Boyden chamber wells and purified neutrophil in the upper compartment. The migrated neutrophil were lysed and detected. The percentages of neutrophil migration were assessed and presented with Chemotaxis Index (CI) value. That is to say, CI= (intensity$_{RISE\ P-8}$−intensity$_{HBSS}$)/(intensity$_{CXCL8}$−intensity$_{HBSS}$)×100%. The result indicates that RISE P-8 effectively antagonize neutrophil response to CXCL8, and competes with CXCL8 for CXCR1 and CXCR2.

EXAMPLE 6

Figure 6A:
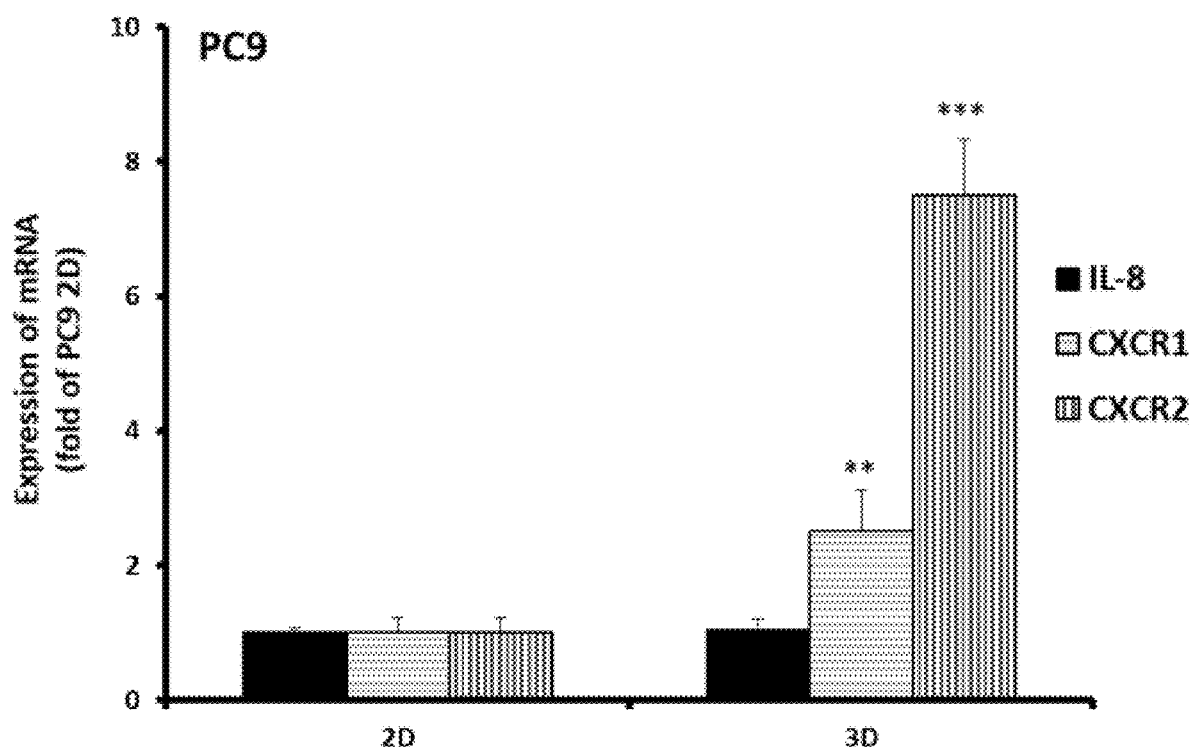
FIG. 6A-6B show the gene expression of IL-8, CXCR1 and CXCR2 increases in 3D (suspended) condition of NSCLC cells.
Figure 6B:
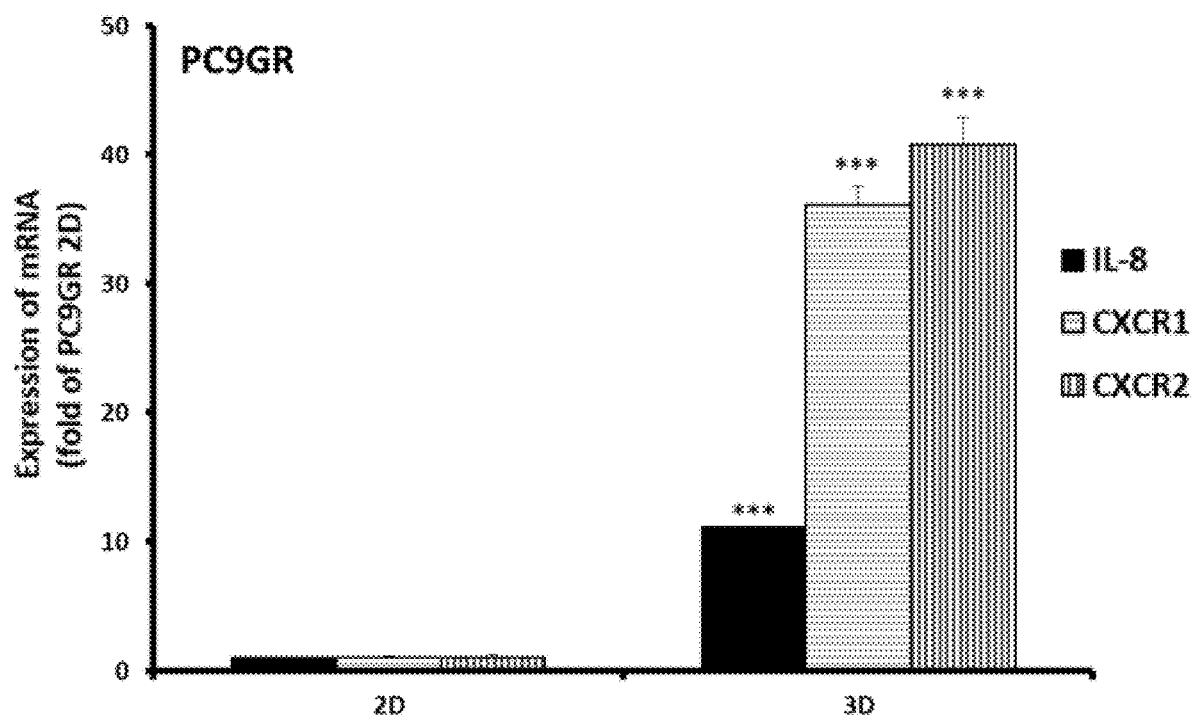

Expression Level of CXCR1, CXCR2 and CXCL8 Genes for Gefitinib-Resistant Cancer Cells Compared with Parental Cancer Cells Survive in Anchorage-Independent Circumstance PC9 (FIG. 6A) and PC9GR (FIG. 6B) show enhanced IL-8 (CXCL8)/CXCR1/CXCR2 mRNA expression in 3D (suspended) culture, compared to 2D. Therefore, CXCL8, CXCR1 and CXCR2 mRNA expression shows different between adhesion situation and suspended situation for cancer cells survival and growth.

EXAMPLE 7

Figure 7A:
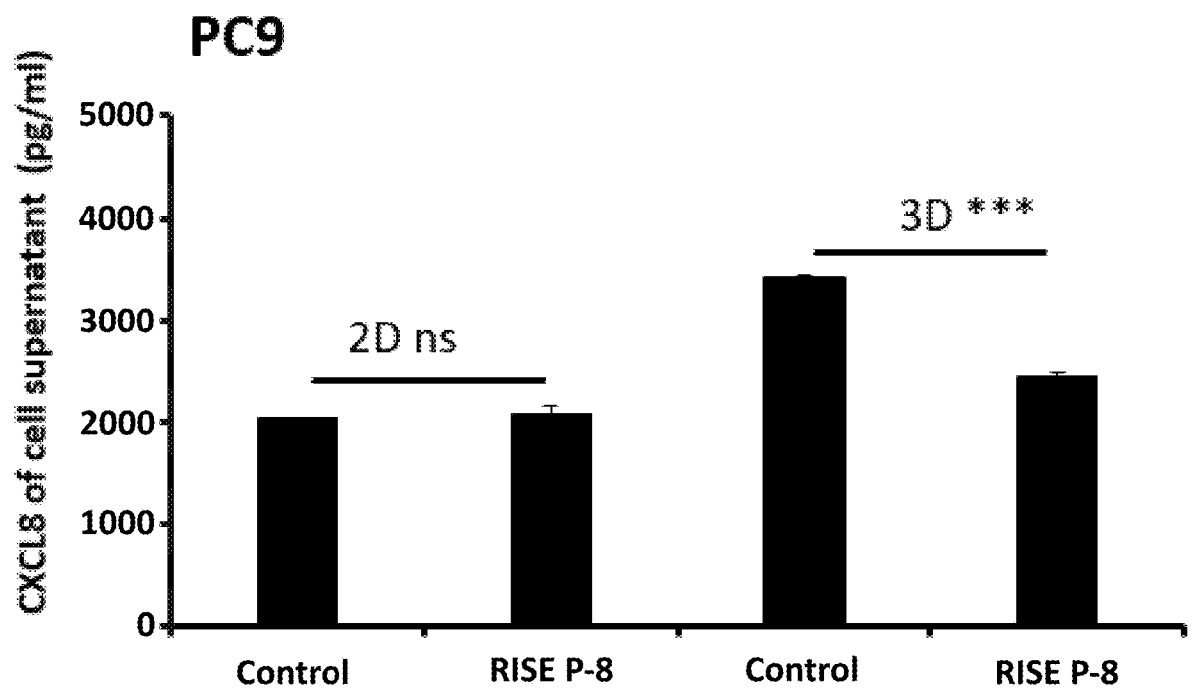
FIG. 7A-7B are representations of RISE P-8 significantly reducing IL-8 protein expression in 3D (suspended) condition of NSCLC cells.
Figure 7B:
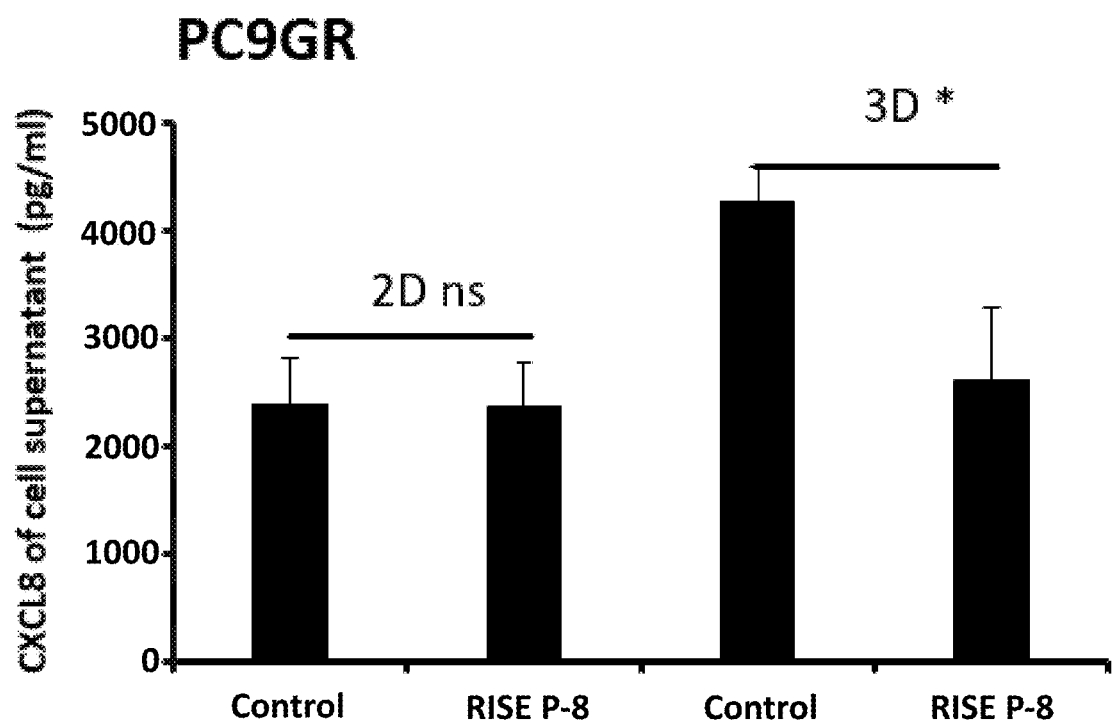

RISE P-8 can Significantly Reduce IL-8 Protein Expression in 3D (Suspended) Condition of NSCLC Cancer Cells Cells underwent serum-free 16-18 hr and suspended into $10^6$ cells/mL in growth medium. $2\times10^6$ cells/well were seeded in coating/non-coating 6 well plates and treated with/without RISE P-8 (200 ng/ml) for 24 hrs. In PC9 (FIG. 7A) and PC9GR (FIG. 7B) it seems RISE P-8 can significantly attenuate IL-8 autocrine only in suspended culture. Data are shown as mean±SD. *P<0.05; ***P<0.001, student's t-test. That is, RISE P-8 treatment can significantly reduce IL-8 secretion of cancer cells surviving in anchorage-independent circumstance.

EXAMPLE 8

Expression Level of CXCR1, CXCR2 and CXCL8 Genes for Gefitinib-Resistant Cancer Cells Treating Gefitinib Compared with Treating Gefitinib Combined with RISE P-8

Figure 8A:
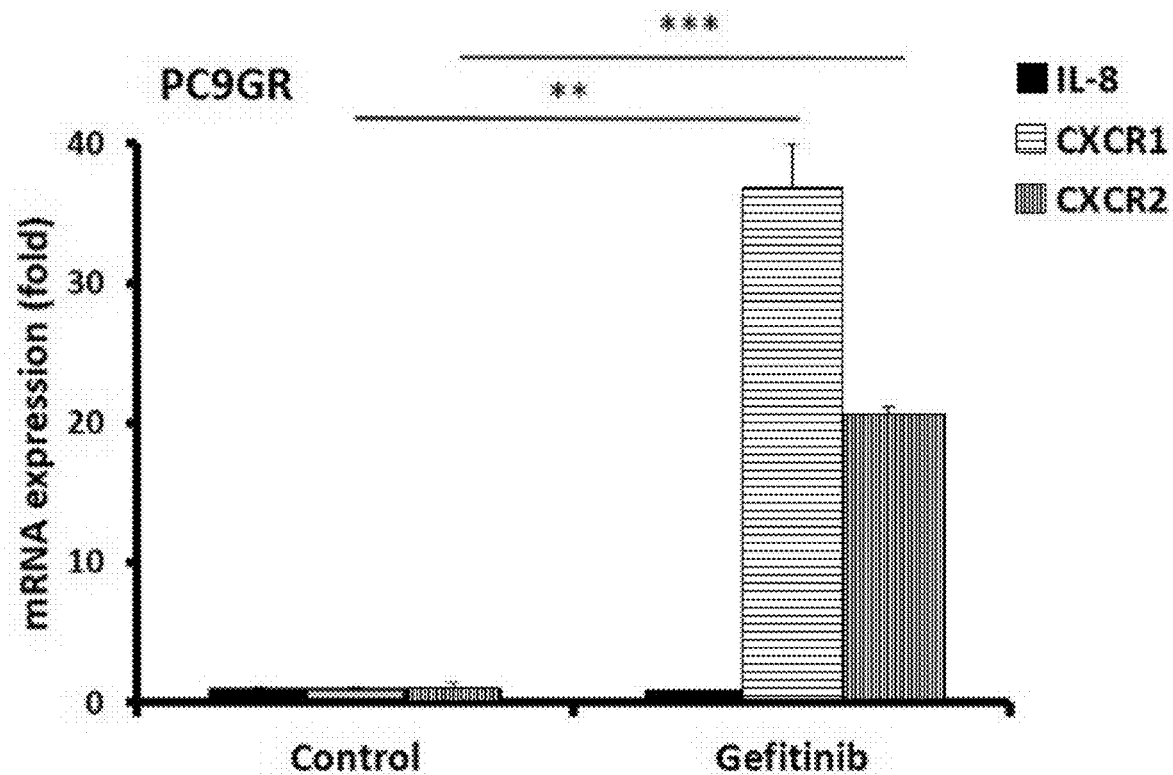
FIG. 8A-8D depict expression level of CXCR1, CXCR2 and CXCL8 genes for Gefitinib-resistant cancer cells treating Gefitinib compared with treating Gefitinib combined with RISE P-8.
Figure 8B:
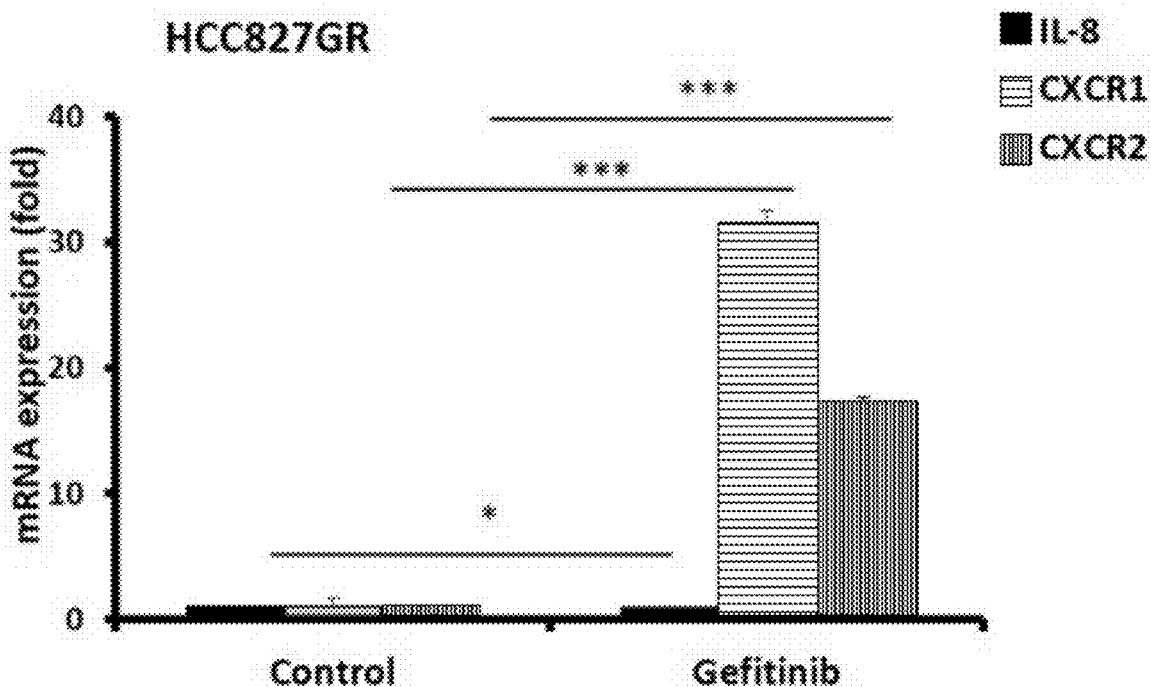
Figure 8C:
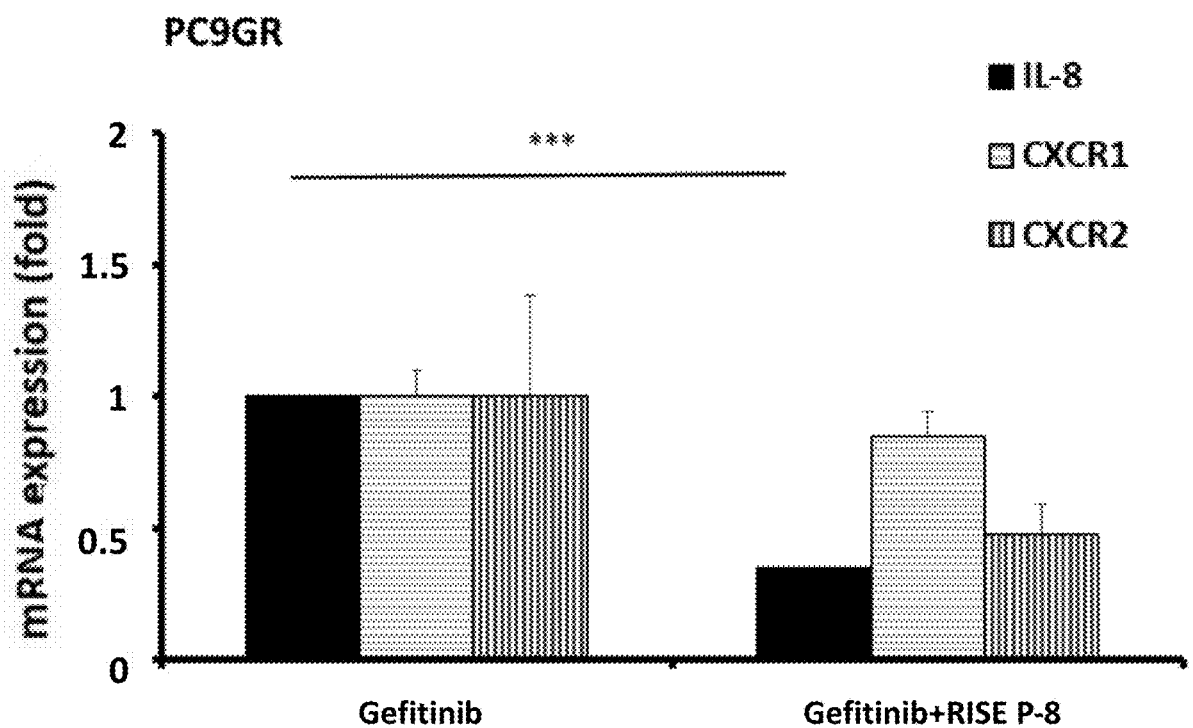
Figure 8D:
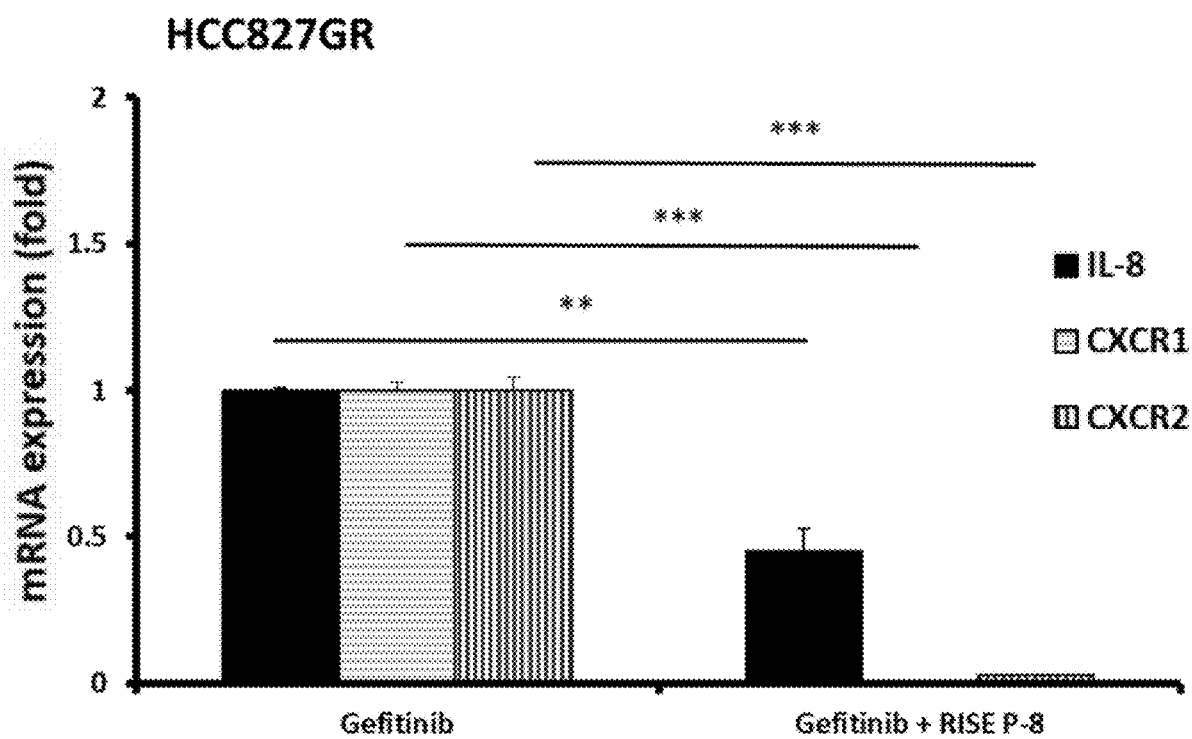

Treating Gefitinib-resistant cancer cells with 5 μM Gefitinib for 24 hrs, mRNA expression of PC9GR (FIG. 8A) and HCC827GR (FIG. 8B) significantly enhanced in IL-8, CXCR1 and CXCR2. However, the Gefitinib-resistant cancer cells are treated by Gefitinib combined with RISE P-8 (200 ng/mL), IL-8, CXCR1 and CXCR2 mRNA expression of PC9GR (FIG. 8C) and HCC827GR (FIG. 8D) are decreased. Data are shown as mean±SD. *<0.05; P<0.01; *P<0.001, student's t-test. That is to say, RISE P-8 can compete with IL-8 and attenuate its feedback to regulate gene expression of IL-8, CXCR1 and CXCR2 decreased.

EXAMPLE 9

Gefitinib-Resistant Cancer Cells are Arrested in G0/G1 Phase Via Treated RISE P-8

Figure 9A:
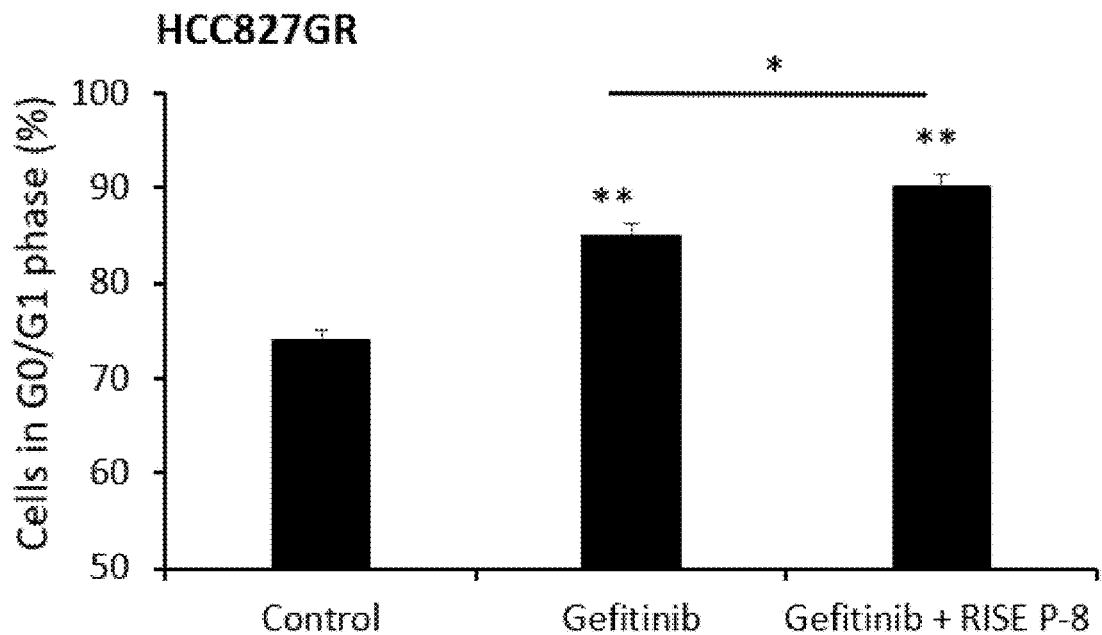
FIG. 9A-9B show cell cycles of Gefitinib-resistant NSCLC cells are arrested in G0/G1 phase by RISE P-8.
Figure 9B:
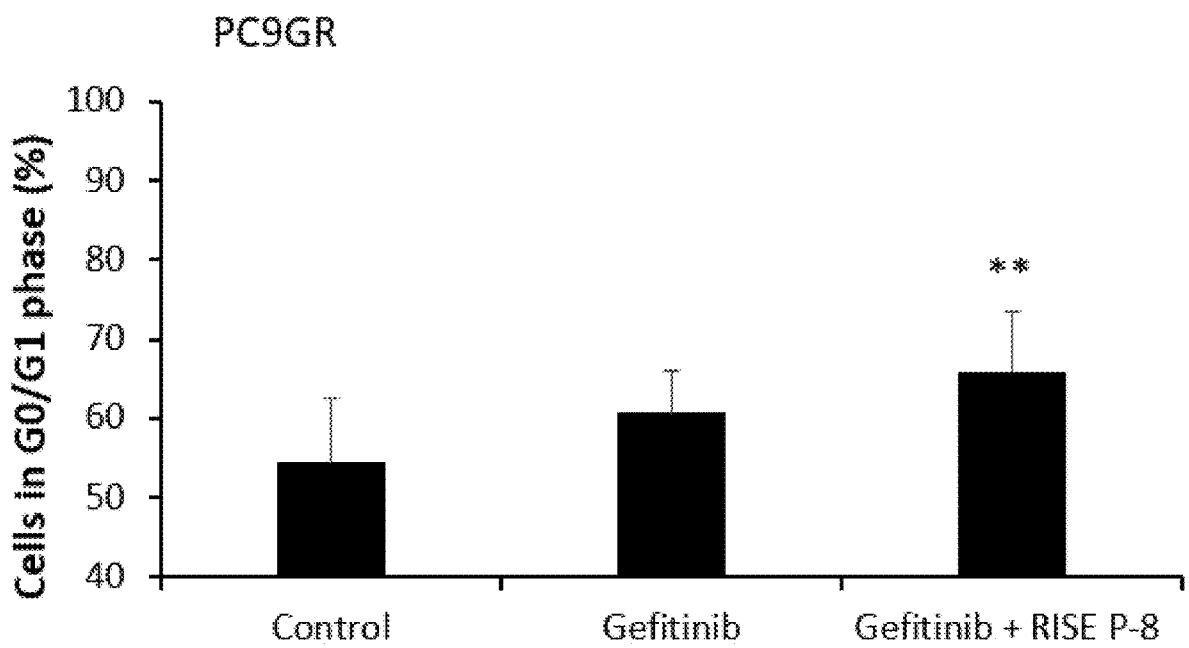

The cancer cells were treated 5 μM Gefitinib or/and RISE P-8 (200 ng/mL) or/and CXCL8 (100 ng/mL) for 24 hours, then cells were harvested and fixed with 75% ice-cold ethanol at 20° C. overnight. After fixation and washed, the cancer cells stained with propidium iodide (PI) and the cell cycle of the cancer cells were analyzed by flow cytometer and FlowJo 7.6.1 for data acquisition and analysis. The present invention illustrated that the cell cycle of HCC827GR (FIG. 9A) and PC9GR (FIG. 9B) arrest in G0/G1 phase. Further, the cell cycle of cancer cells can arrest much more significantly the percentage of G0/G1 phase of total cells via Gefitinib and RISE P-8 co-treated than Gefitinib treated along (FIG. 9A and FIG. 9B). Data are shown as mean±SD. *P<0.05; P<0.01; *P<0.001, student's t-test. That is, the present invention infers RISE P-8 co-treat with Gefitinib can trigger cells apoptosis and reduce the cell proliferation.

EXAMPLE 10

The Anchorage-Independent Proliferation Rate of Gefitinib-Resistant Cancer Cells can be Inhibited by RISE P-8

Figure 10A:
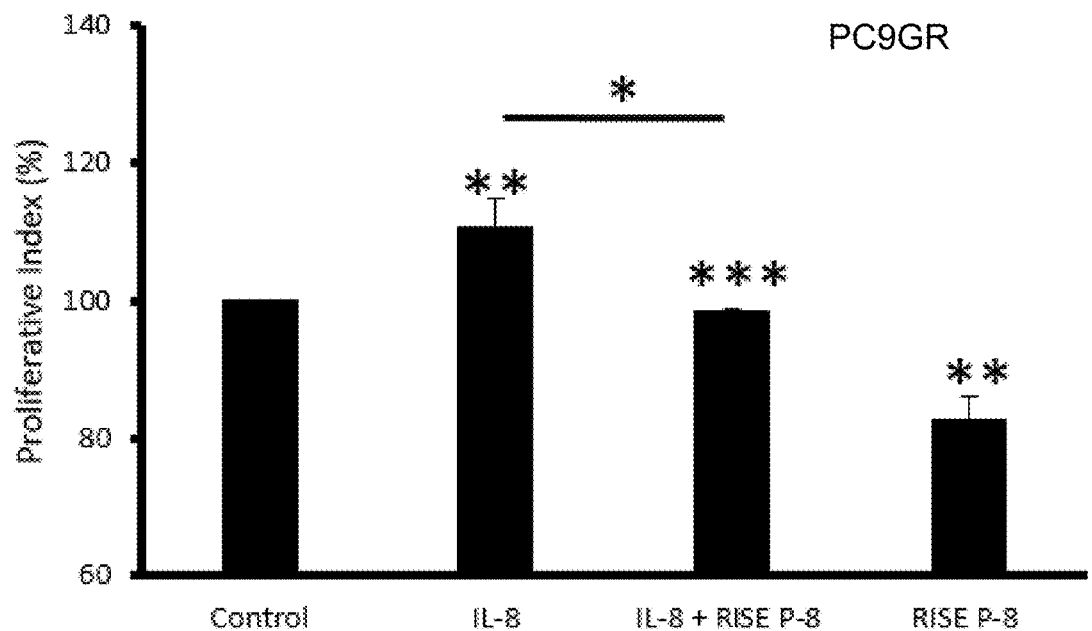
FIG. 10A-10B illustrate RISE P-8 can inhibit anchorage-independent proliferation rate of Gefitinib-resistant NSCLC cell lines when treated with/without IL-8 simultaneously.
Figure 10B:
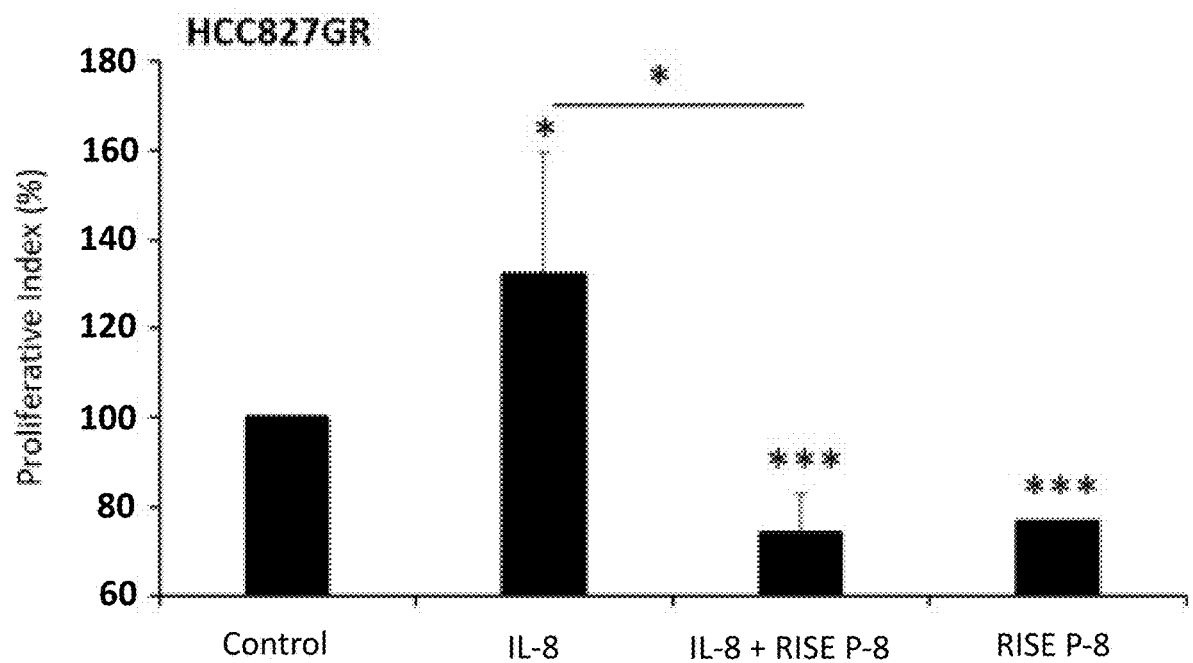

Cell proliferation assay was performed using cell counting kit-8 (CCK-8) (Dojindo, Kumamoto, Japan). The Gefitinib-resistant cancer cells treated by Gefitinib (5 μM) with RISE P-8 (200 ng/mL), or treated by Gefitinib with RISE P-8 and IL-8 (100 ng/mL) for 24 hours. The proliferative rate of Gefitinib-resistant cancer cells significantly attenuated in PC9GR (FIG. 10A) and HCC827GR (FIG. 10B), compared with control and IL-8 group (FIG. 10A and FIG. 10B). Data are shown as mean±SD. *P<0.05; P<0.01; *P<0.001, student's t-test. These data further confirm that cancer cells co-treated with Gefitinib and RISE P-8 resulted in down-regulation of CXCL8, CXCR1 and CXCR2.

EXAMPLE 11

RISE P-8 can Inhibit Long-Term Growth in Gefitinib-Resistant Cancer Cells

Figure 11A:
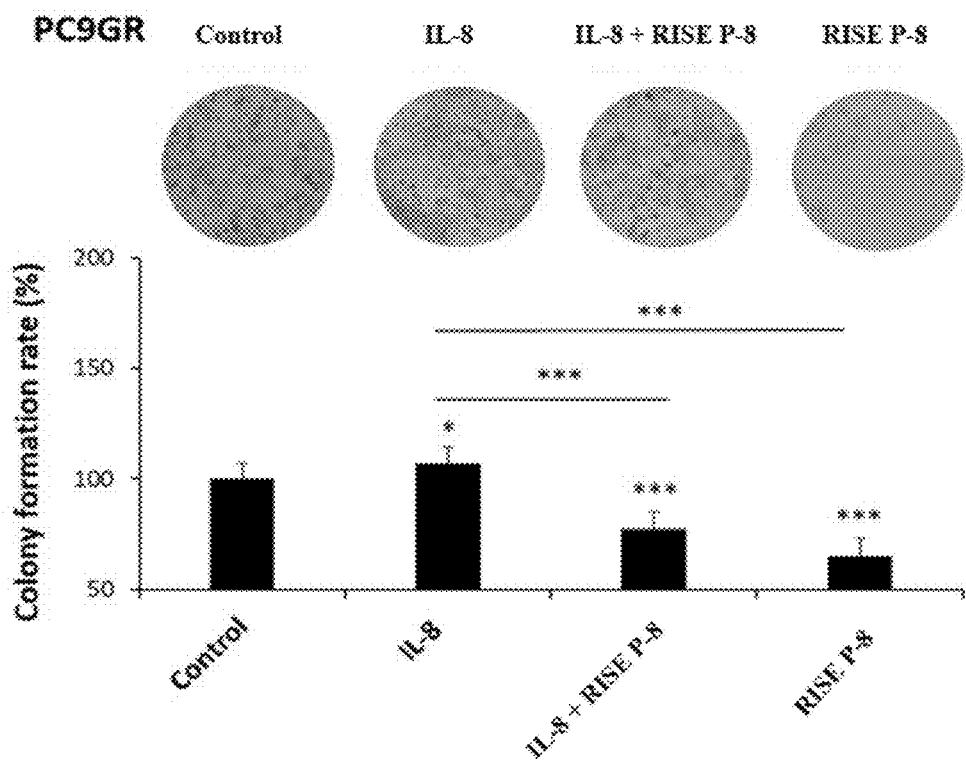
FIG. 11A-11B illustrate RISE P-8 can inhibit long-term growth in Gefitinib-resistant NSCLC cells.
Figure 11B:
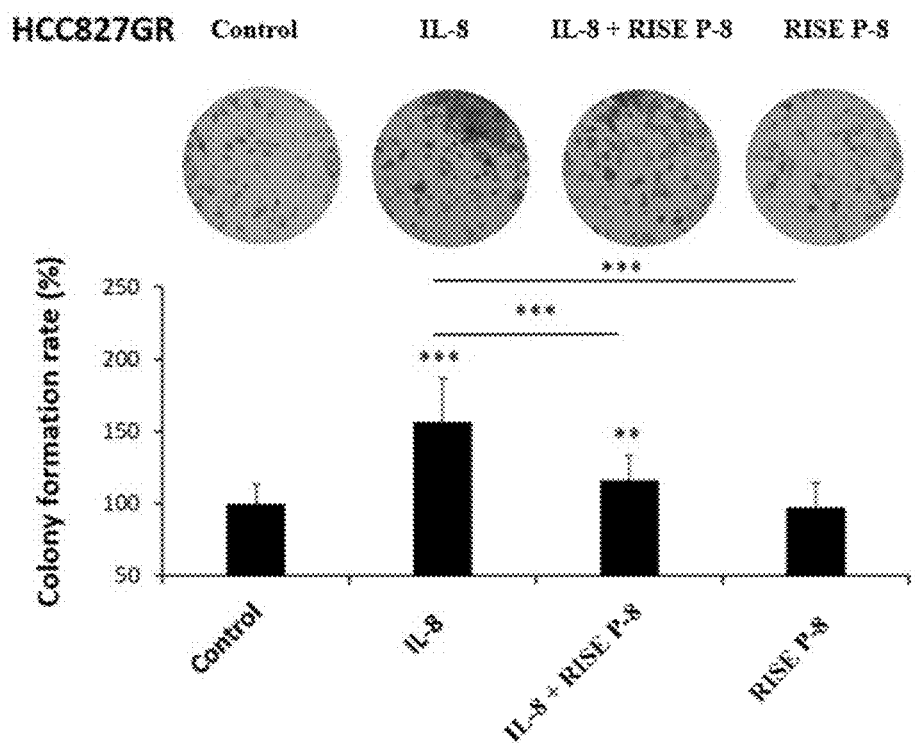

On the other side, the Gefitinib-resistant cancer cells treated by Gefitinib (5 μM) with RISE P-8 (200 ng/mL), or treated by Gefitinib with RISE P-8 and IL-8 (100 ng/mL), or treated by Gefitinib with IL-8 respectively for colony formation assay. The colony formation assay was also performed to evaluate cell proliferation. These results reveal that the colony formation rate of the cells treated by RISE P-8 slow down significantly than control group and IL-8 group in PC9GR (FIG. 11A) and HCC827GR (FIG. 11B) in long term. Data are shown as mean±SD. *P<0.05; P<0.01; *P<0.001, student's t-test.

EXAMPLE 12

RISE P-8 can Inhibit the Invasion Ability of Gefitinib-Resistant Lung Adeno Carcinoma Cells The invasion ability of cell was performed by using 8 µm pore size transwell (Corning FluoroBlok™). The transwell insert was coated with 60 µl matrigel (300 µg/ml in serum-free medium, BD Bioscience) overnight at 37° C. in 5% $CO_2$ atmosphere. $2.5 \times 10^4$ cells in 0.2 mL of serum-free growth medium were seeded into the upper chamber coated with matrigel and then treated with drugs IL-8 (100 ng/ml) with/without RISE P-8 (200 ng/ml). After incubation for 24 hrs at 37° C. in 5% $CO_2$, membrane of upper chamber was fixed with methanol and stained with propidium iodide (PI). The invasive cells in the bottom of membrane were imaged and counted by using an inverted fluorescence microscope (Observer.Z1, Zeiss) in five random fields of each specimen (magnification, ×100).

The Gefitinib-resistant cancer cells treated by Gefitinib (5 µM) with RISE P-8 (200 ng/mL), or treated by Gefitinib with RISE P-8 and IL-8 (100 ng/mL), or treated by Gefitinib with IL-8 respectively for invasion ability assay.

Figure 12A:
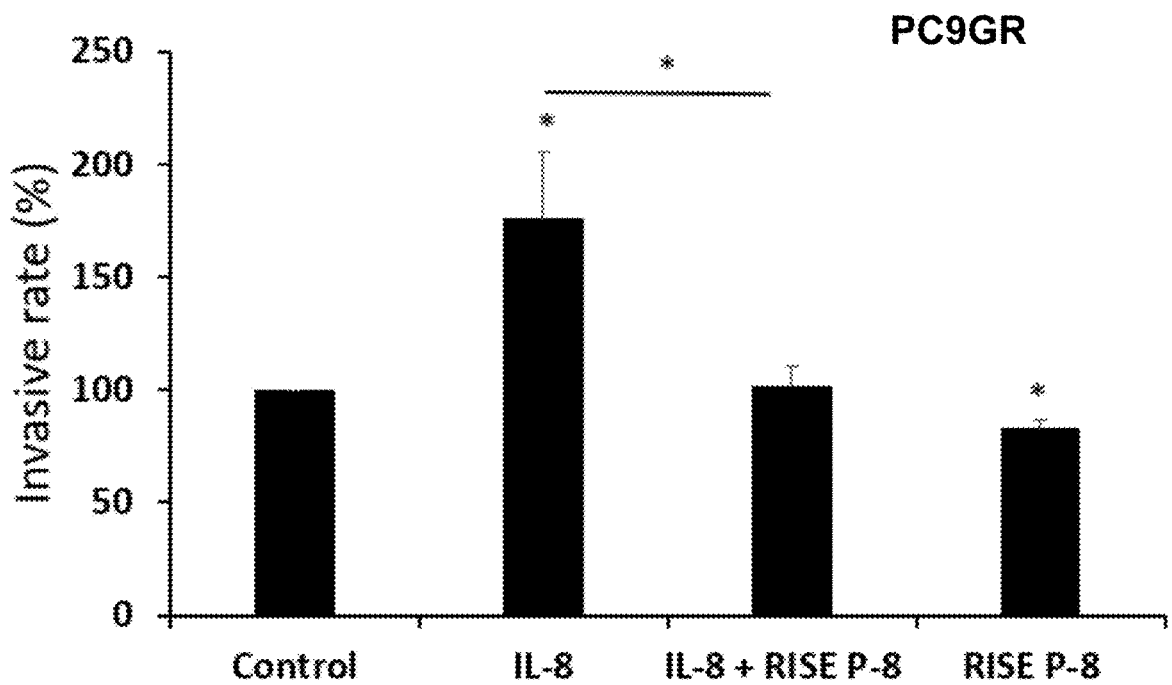
FIG. 12A-12B illustrate RISE P-8 can inhibit the invasion ability of Gefitinib-resistant NSCLC cells.
Figure 12B:
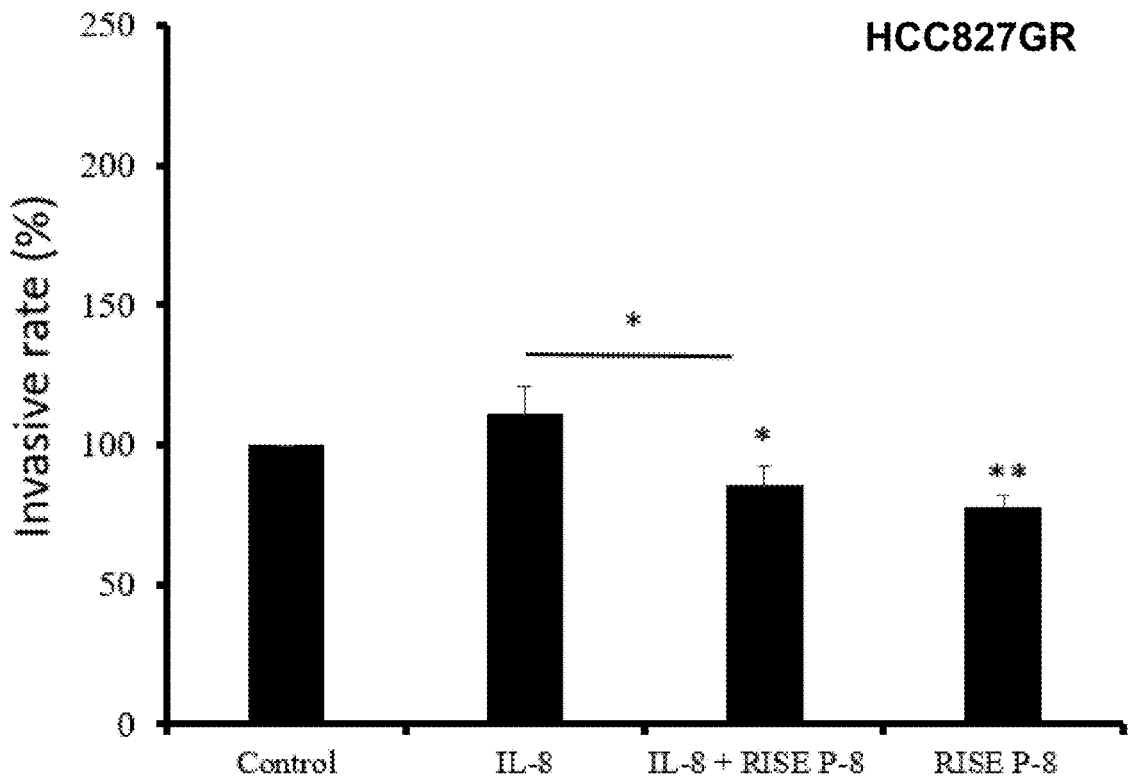

The results of transwell invasion assays show RISE P-8 decreases invasion rate compared with control group in PC9GR (FIG. 12A) and HCC827GR (FIG. 12B). Meanwhile, it can prevent significantly invasion rate of "IL-8+RISE P-8 group" in PC9GR (FIG. 12A) and HCC827GR (FIG. 12B) compared with "IL-8 group" in PC9GR (FIG. 12A) and HCC827GR (FIG. 12B). Data are shown as mean±SD. *P<0.05; **P<0.01, student's t-test.

EXAMPLE 13

Figure 13A:
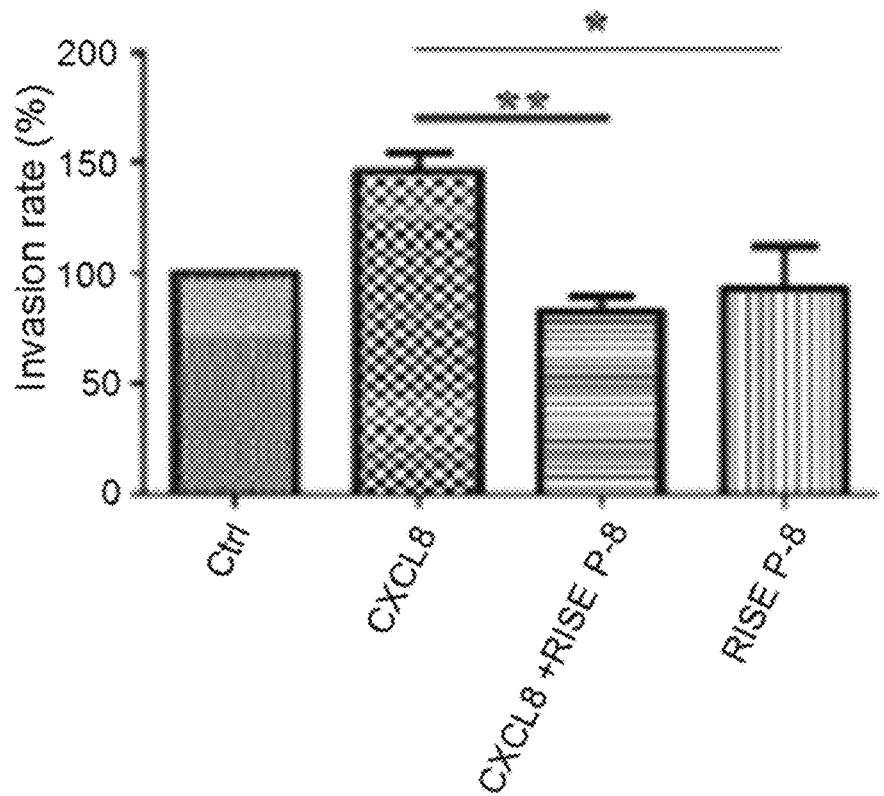
FIG. 13A-13B illustrate RISE P-8 can suppress the invasion ability in Lewis Lung carcinoma cells.
Figure 13B:
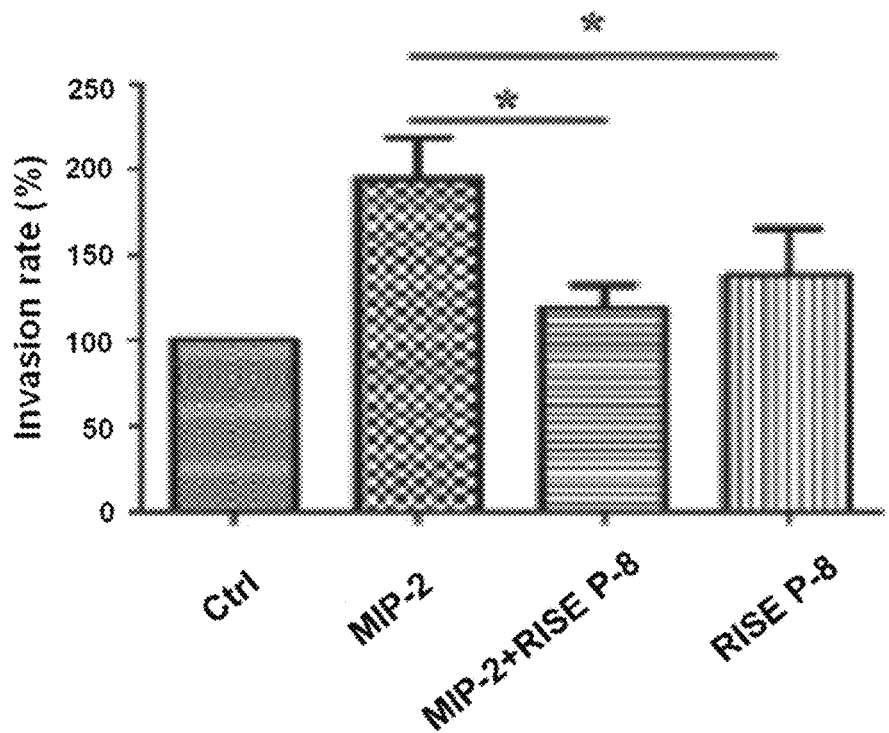

Suppressing Effects of RISE P-8 on the Invasion Ability in Lewis Lung Carcinoma Cells Please refer to FIG. 13A and FIG. 13B, the present invention also represented invasion of LL/2 cells (Louis lung carcinoma) treated with CXCL8, MIP-2 or RISE P-8. The character of LL/2 cancer cell is very prone to invasion into lung and grows rapidly. The LL/2 cells were seeded onto Matrigel-coated polycarbonate filters to analyze their invasive potentials. The cells were then incubated for 24 hr in chambers and were analyzed by staining PI and counted under a microscope. Representative fields of invasive cells on the transwell membrane (at 100× magnification) and the invasion rate were shown. The LL/2 cells treated with CXCL8 (100 ng/ml), RISE P-8 (200 ng/ml), or MIP-2 (50 ng/ml) respectively. The FIG. 13A-13B showed the quantitative presentation of invasion rate. Data are shown as mean±SD. *P<0.05; **P<0.01, student's t-test. The same results were showed in the data of MIP-2 induced cell invasion (FIG. 13B). MIP-2 is the CXCL8 homologues in murine. RISE P-8 also significantly decreased the number of invasive cells. That is, the present invention further illustrated that CXCL8 could excite LL/2 invasion ability, whereas RISE P-8 significantly suppressed CXCL8 stimulated cell invasion.

EXAMPLE 14

Figure 14A:
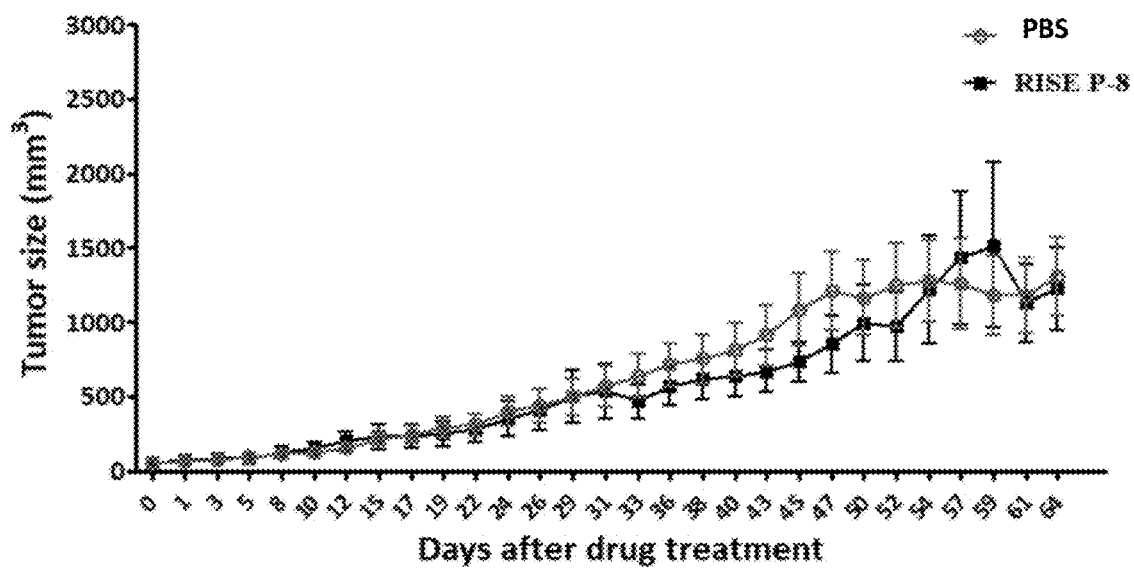
FIG. 14A-14D illustrate RISE P-8 and Gefitinib combined usage inhibits tumor growth and prolongs lifespan in vivo.
Figure 14B:
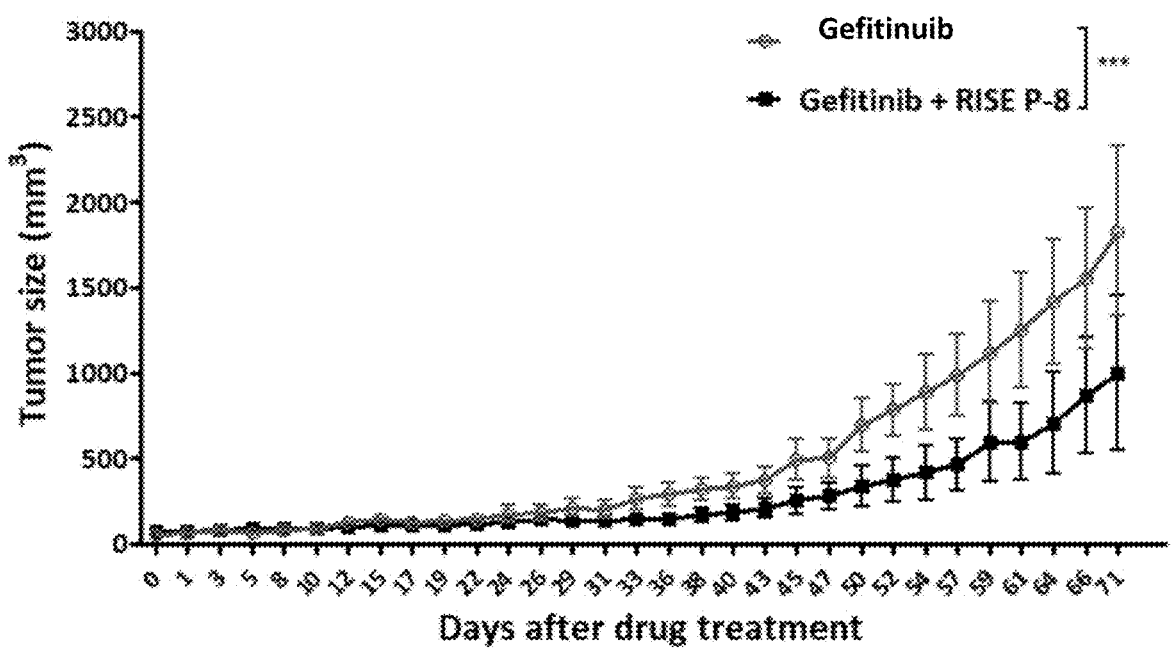
Figure 14C:
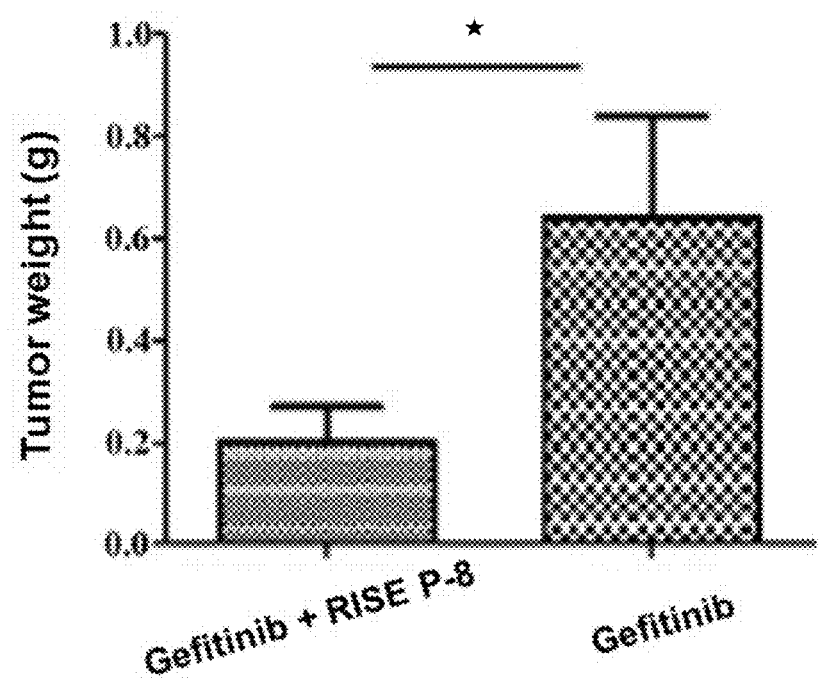
Figure 14D:
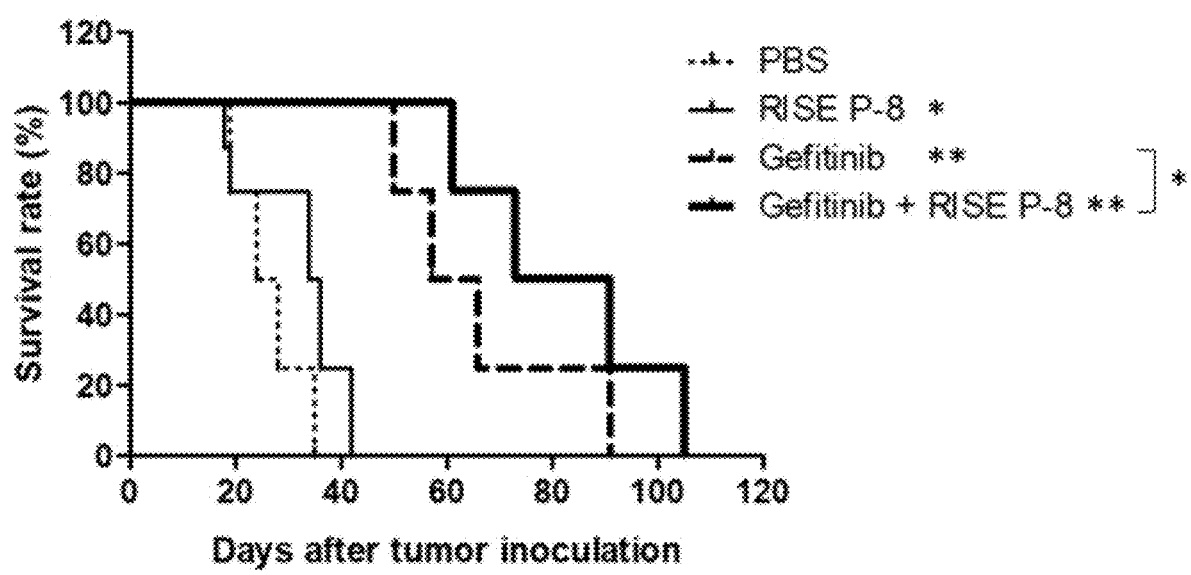

RISE P-8 and Gefitinib Combined Usage Inhibits Tumor Growth and Prolongs Lifespan In Vivo Male BALB/c nude mice (5-week old) were purchased from National Laboratory Animal Center. PC9GR were subcutaneously inject in back of BALB/c nude mice. RISE P-8 (500 µg/kg) was i.p. injected three times and Gefitinib (80 mg/kg) was administered by oral gavage twice weekly. The tumor size of tumor-bearing mice were recorded after treatment until Day 72. Tumor size were significantly inhibited in "Gefitinib+RISE P-8 group" (FIG. 14A-14B). That is, the results show RISE P-8 combined with Gefitinib significantly reduces tumor size compared to "Gefitinib group", and also effectively prolongs lifetime of tumor-bearing mice for more than 14 days compared to the others group at least (FIG. 14C).

EXAMPLE 15

Figure 15A:
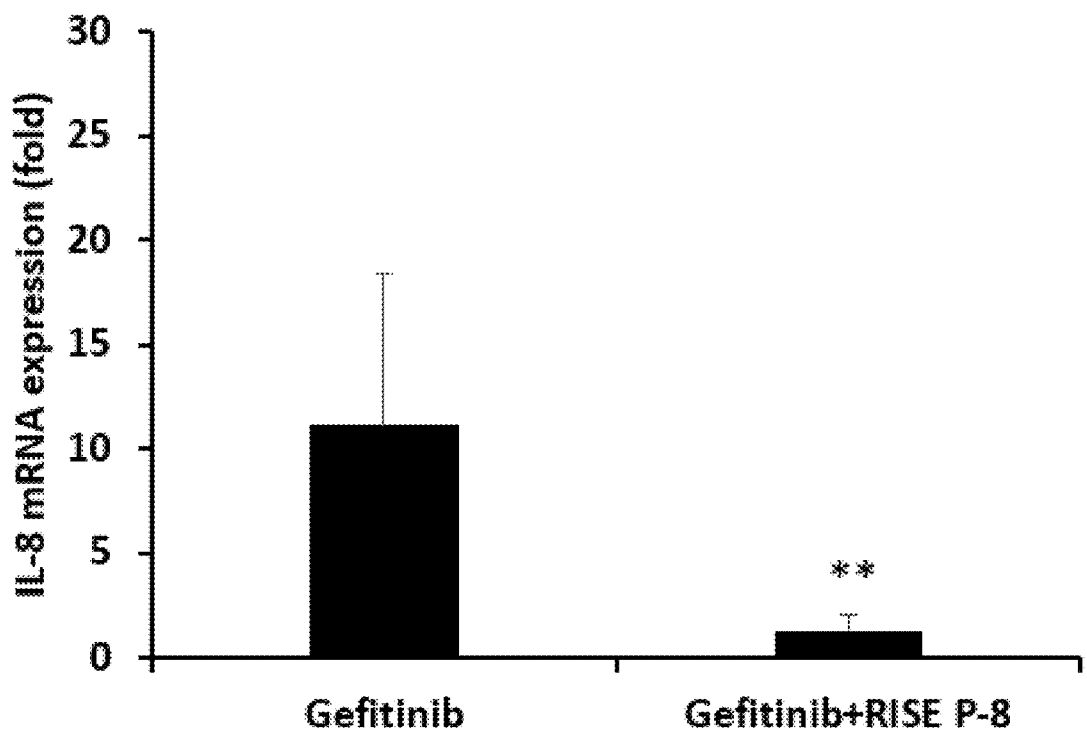
FIG. 15A-15C show RISE P-8 and Gefitinib combined usage attenuates IL-8, CXCR1 and CXCR2 mRNA expression in vivo.
Figure 15B:
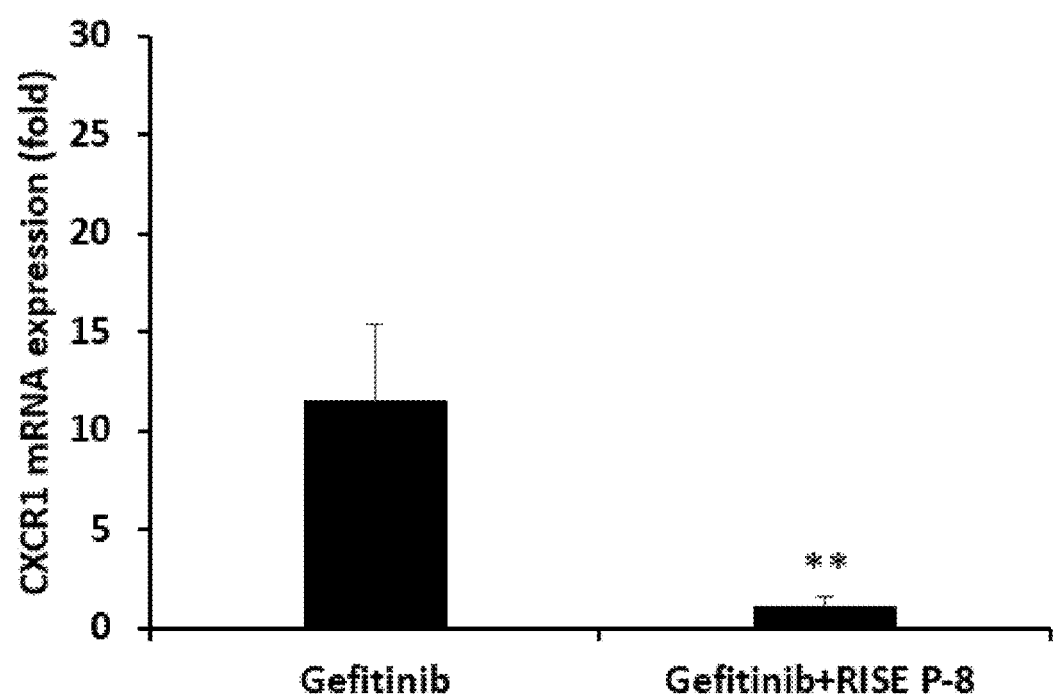
Figure 15C:
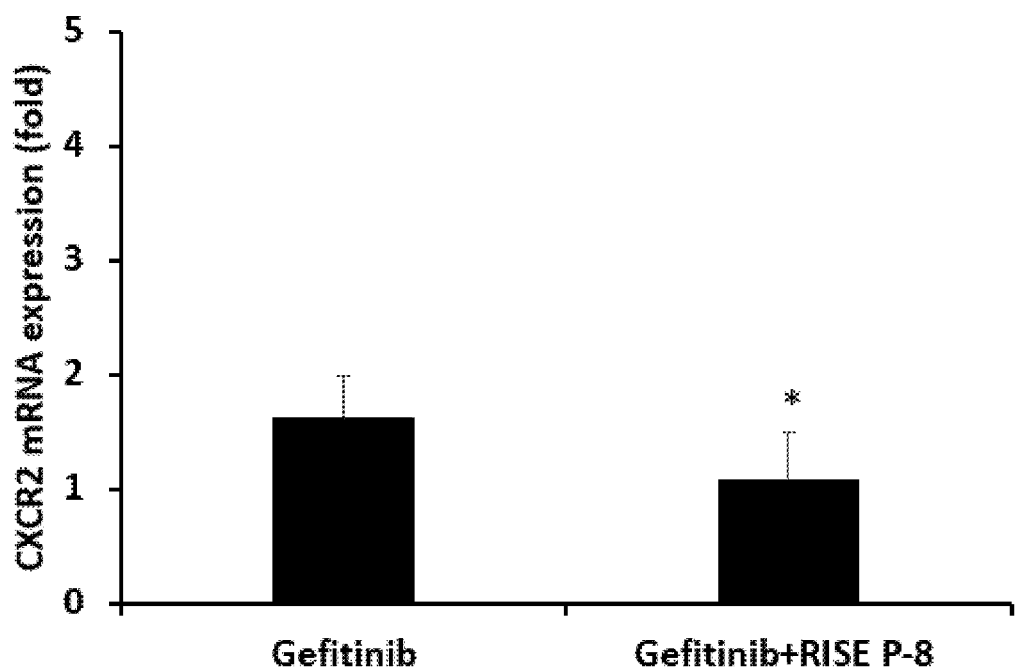

RISE P-8 and Gefitinib Combined Usage Attenuates IL-8, CXCR1 and CXCR2 mRNA Expression In Vivo After PC9GR tumor-bearing BALB/c nude mice were sacrificed at Day 72, the IL-8, CXCR1 and CXCR2 gene expressions of tumor tissue are examined in "Gefitinib" group and "Gefitinib+RISE P-8 group" (FIG. 15A-15C). Data are shown as mean±SEM (n=8). *P<0.05; P<0.01; *P<0.001, student's t-test.

In summary, the pharmaceutical composition attenuate expression of IL-8, CXCR1, CXCR2 in tumor microenvironment via synergistic effect, inhibits tumor growth via downregulating IL-8, blocks cancer cell migration and invasion via downregulating IL-8, and treats metastases or reduces metastatic spread. Further, the above-mentioned drug-resistant cell over-expresses IL-8.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

As indicated, these modifications may be made to the invention in light of the foregoing description of illustrated embodiments of the invention and are to be included within the spirit and scope of the invention. Thus, while the invention has been described herein with reference to particular embodiments thereof, a latitude of modification, various changes, and substitutions are intended in the foregoing disclosures. It will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the invention.

What is claimed is:

1. A method for treating a cancer, comprising:

administering a pharmaceutical composition in a therapeutically effective amount according to a gefitinib-resistant cancer subject in need thereof, wherein the cancer is resistant to gefitinib, wherein the cancer is non-small cell lung cancer, wherein the pharmaceutical composition comprises a chemokine analogue peptide and a medicament, wherein the chemokine analogue peptide is RISE P-8 as set forth in SEQ ID NO:1, wherein the medicament comprises gefitinib and a pharmaceutically acceptable buffer, diluent, carrier, adjuvant or excipient.

2. The method according to claim 1, wherein the therapeutically effective amount of the RISE P-8 set forth in SEQ ID NO:1 is from about 0.01 mg/kg to about 500 mg/kg body weight per dose.

3. The method according to claim 1, wherein the gefitinib-resistant cancer subject is selected from mammals, wherein the mammals are selected from cat, dog, rabbit, cattle, horse, sheep, goat, monkey, mouse, rat, gerbil, guinea pig, pig and human.

* * * * *

SEQUENCE LISTING

<160> NUMBER OF SEQ ID NOS: 7

<210> SEQ ID NO 1
<211> LENGTH: 72
<212> TYPE: PRT
<213> ORGANISM: Artificial Sequence
<220> FEATURE:
<223> OTHER INFORMATION: RISE P-8

<400> SEQUENCE: 1

Gly Ser Lys Glu Leu Arg Cys Gln Cys Ile Arg Ser Tyr Ser Lys Pro
1               5                   10                  15

Phe His Pro Lys Phe Ile Lys Glu Leu Arg Val Ile Pro Ala Ser Gln
            20                  25                  30

Phe Cys Ala Asn Thr Glu Ile Ile Val Lys Leu Ser Asp Gly Arg Glu
        35                  40                  45

Leu Cys Leu Asp Pro Lys Glu Asn Trp Val Gln Arg Val Val Glu Lys
    50                  55                  60

Phe Leu Lys Arg Ala Glu Asn Ser
65                  70

<210> SEQ ID NO 2
<211> LENGTH: 21
<212> TYPE: DNA
<213> ORGANISM: Artificial Sequence
<220> FEATURE:
<223> OTHER INFORMATION: forward primer for CXCL8

<400> SEQUENCE: 2
gagcactcca taaggcacaa a                                           21

<210> SEQ ID NO 3
<211> LENGTH: 18
<212> TYPE: DNA
<213> ORGANISM: Artificial Sequence
<220> FEATURE:
<223> OTHER INFORMATION: reverse primer for CXCL8

<400> SEQUENCE: 3
atggttcctt ccggtggt                                               18

<210> SEQ ID NO 4
<211> LENGTH: 20
<212> TYPE: DNA
<213> ORGANISM: Artificial Sequence
<220> FEATURE:
<223> OTHER INFORMATION: forward primer for CXCR1

<400> SEQUENCE: 4
gaccaacatc gcagacacat                                             20

<210> SEQ ID NO 5
<211> LENGTH: 20
<212> TYPE: DNA
<213> ORGANISM: Artificial Sequence
<220> FEATURE:
<223> OTHER INFORMATION: reverse primer for CXCR1

<400> SEQUENCE: 5
tgcttgtctc gttccacttg                                             20

<210> SEQ ID NO 6
<211> LENGTH: 25
<212> TYPE: DNA

```
<213> ORGANISM: Artificial Sequence
<220> FEATURE:
<223> OTHER INFORMATION: forward primer for CXCR2

<400> SEQUENCE: 6
ggctaagcaa aatgtgatat gtacc                                              25

<210> SEQ ID NO 7
<211> LENGTH: 20
<212> TYPE: DNA
<213> ORGANISM: Artificial Sequence
<220> FEATURE:
<223> OTHER INFORMATION: reverse primer for CXCR2

<400> SEQUENCE: 7
caaggttcgt ccgtgttgta                                                    20
```